US009796985B2

(12) United States Patent
Schaller et al.

(10) Patent No.: US 9,796,985 B2
(45) Date of Patent: Oct. 24, 2017

(54) COMPOSITIONS AND METHOD FOR MODULATING THE SENSITIVITY OF PLANTS TO CYTOKININ

(71) Applicants: Trustees of Dartmouth College, Hanover, NH (US); The University of North Carolina at Chapel Hill, Chapel Hill, NC (US)

(72) Inventors: G. Eric Schaller, Lebanon, NH (US); Hyo-Jung Kim, White River Junction, VT (US); Joseph Kieber, Chapel Hill, NC (US)

(73) Assignees: Trustees of Dartmouth College, Hanover, NH (US); The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/777,806

(22) PCT Filed: Mar. 18, 2014

(86) PCT No.: PCT/US2014/030953
§ 371 (c)(1),
(2) Date: Sep. 17, 2015

(87) PCT Pub. No.: WO2014/153310
PCT Pub. Date: Sep. 25, 2014

(65) Prior Publication Data
US 2016/0289698 A1 Oct. 6, 2016

Related U.S. Application Data

(60) Provisional application No. 61/803,606, filed on Mar. 20, 2013.

(51) Int. Cl.
C12N 15/82 (2006.01)

(52) U.S. Cl.
CPC ..... *C12N 15/8295* (2013.01); *C12N 15/8227* (2013.01); *C12N 15/8261* (2013.01)

(58) Field of Classification Search
None
See application file for complete search history.

(56) References Cited

U.S. PATENT DOCUMENTS

| | | | | |
|---|---|---|---|---|
| 7,619,146 B2 * | 11/2009 | Frankard | ............... | C12N 9/0032 435/419 |
| 7,807,869 B1 | 10/2010 | Schnabel et al. | ............. | 800/278 |
| 8,222,483 B2 | 7/2012 | Brugiere et al. | ............... | 800/278 |
| 2004/0123343 A1 * | 6/2004 | La Rosa | .............. | C07K 14/415 800/278 |
| 2006/0107345 A1 * | 5/2006 | Alexandrov | ......... | C07K 14/415 800/278 |
| 2007/0050867 A1 | 3/2007 | Harada et al. | ................ | 800/287 |
| 2009/0061519 A1 | 3/2009 | Turano et al. | ................ | 435/419 |
| 2011/0214199 A1 * | 9/2011 | Coffin | ................ | C12N 15/1079 800/275 |
| 2012/0216318 A1 | 8/2012 | LaRosa et al. | ............... | 800/298 |

OTHER PUBLICATIONS

UniProtKB/Swiss-Prot., ID FK126__ARATH, AC Q9LMR5; Oct. 1, 2000, RecName: Full=F-box/kelch-repeat-protein At1g15670.*
UniProtKB/Swiss-Prot., ID SKI20__ARATH DT Oct. 1, 2000, AC Q9M1Y1; Q8L991, RecName: Full=F-box/kelch-repeat protein SKIP20, Name=SKIP20; OrderedLocusNames=At3g59940.*
Kim et al, Plant Signaling and Behavior, vol. 8, No. 12, Dec. 2013, electronic publication e264.pdf.*
Kim et al, PNAS, Jun. 11, 2013, vol. 110, No. 24, pp. 10028-10033. pdf.*
Argyros et al. "Type B response regulators of Arabidopsis play key roles in cytokinin signaling and plant development" Plant Cell 2008 20(8):2102-2116.
Brugiere et al. "Cytokinin oxidase gene expression in maize is localized to the vasculature, and is induced by cytokinins, abscisic acid, and abiotic stress" Plant Physiol. 2003 132:1228-1240.
Dharmasiri et al. "The F-box protein TIR1 is an auxin receptor" Nature 2005 435(7041):441-445.
Houba-Herin et al. "Cytokinin oxidase from *Zea mays*: purification, cDNA cloning and expression in moss protoplasts" Plant J. 1999 17:615-626.
Hua & Vierstra "The cullin-RING ubiquitin-protein ligases" Annu. Rev. Plant Biol. 2011 62:299-334.
Hwang et al. "Cytokinin signaling networks" Annu. Rev. Plant Biol. 2011 63:353-380.
Inoue et al. "Identification of CRE1 as a cytokinin receptor from Arabidopsis" Nature 2001 409(6823):1060-1063.
Kim et al. "Cytokinin-mediated control of leaf longevity by AHK3 through phosphorylation of ARR2 in Arabidopsis" Proc. Natl. Acad. Sci. U.S.A. 2006 103(3):814-819.
Kim et al. "Cytokinin-facilitated proteolysis of Arabidopsis Response Regulator 2 attenuates signaling output in two-component circuitry" Plant J. 2012 69(6):934-945.
Morris et al. "Isolation of a gene encoding a glycosylated cytokinin oxidase from maize" Biochem. Biophys. Res. Commun. 1999 255:328-333.
Perilli et al. "The molecular basis of cytokinin function" Curr. Opin. Plant Biol. 2010 13(1):21-26.
Pils & Heyl "Unraveling the evolution of cytokinin signaling" Plant Physiol. 2009 151(2):782-791.

(Continued)

*Primary Examiner* — Eileen O Hara
(74) *Attorney, Agent, or Firm* — Licata & Tyrrell P.C.

(57) ABSTRACT

The present invention includes an expression cassette containing a polynucleotide encoding a polypeptide; and a host cell, transgenic plant (e.g., a dicot or monocot), transformed seed, and transgenic rootstock containing said expression cassette. Methods for desensitizing a plant to endogenous cytokinin; increasing seed, embryo or cotyledon size or weight; increasing the seed yield of a plant; and/or increasing the size of the root or root meristem or formation of lateral or adventitious roots are provided. In some embodiments, expression of the polypeptide is under control of a seed-preferred, embryo-preferred or root-preferred promoter.

13 Claims, 4 Drawing Sheets

(56) References Cited

OTHER PUBLICATIONS

Santner A. & Estelle M. "The ubiquitin-proteasome system regulates plant hormone signaling" Plant J. 2010 61(6):1029-1040.
Schaller et al. "Two-component systems and their co-option for eukaryotic signal transduction" Curr. Biol. 2011 21(9):R320-330.
Smalle et al. "Cytokinin growth responses in Arabidopsis involve the 26S proteasome subunit RPN12" Plant Cell 2002 14(1):17-32.
To et al. "Type-A Arabidopsis response regulators are partially redundant negative regulators of cytokinin signaling" Plant Cell 2004 16(3):658-671.
To et al. "Cytokinin regulates type-A Arabidopsis Response Regulator activity and protein stability via two-component phosphorelay" Plant Cell 2007 19(12):3901-3914.
Tsai et al. "Characterization of genes involved in cytokinin signaling and metabolism from rice" Plant Physiol. 2012 158(4):1666-1684.
Ueguchi et al. "The AHK4 gene involved in the cytokinin-signaling pathway as a direct receptor molecule in Arabidopsis thaliana" Plant Cell Physiol. 2001 42(7):751-755.
Zheng et al. "Auxin Up-Regulated F-BOX Protein1 regulates the cross talk between auxin transport and cytokinin signaling during plant root growth" Plant Physiol. 2011 156(4):1878-1893.
Rice Genome Annotation Project Gene ID Os06g39370 downloaded Sep. 28, 2015.
Seq ID No. 823, US 2011/0214199 A1 (Coffin) Sep. 1, 2011.
Internationl Search Report and Written Opinion in PCT/2014/030953 dated Aug. 28, 2014.
Internationl Preliminary Report on Patentability in PCT/2014/030953 dated Sep. 22, 2015.

* cited by examiner

```
1  ---------------MELIPNLPDDVARECLLRSSYQQFPVIASVCRAWNREVSLSQFL
2  ---------------MELIPDLPETVAYECLLRSSYKQFPLMASVCKLWQREISLSDFF
3  MTMEVSKKKGGDFQQCHELIPGLPSELALECLVRVPFQFQSAMRSVCRSWRSLLSDSSFI
4  --MGVSKKKSG--EIRGDLIPGLPEELAIECLVRVPFQFHSSIKSVCRSWKCVISSRSFI
                   *** **   * ***  *        ***  *   *     *

1  HQRKASRHSQELLILSQARVDPAGSGK------------------------------IIATP
2  RHRKASGHSQELVVLSQARVDPVKELVSGN---------------------------KTIPTP
3  QERRRCGKTELLLCLVQPLTPPIPASKSVDETLMVDEKKSEDES--------HPRVFCTP
4  KERIGFGKAESLLCLVQPLTSPPSPAMMEGGEMSQKKKEEEEGESQMTQQLLQPRITGTP
       *      *  *  *                                        **

1  EYRISVLESGSGLWTELPPIPGQTKGLPLFCRLVSVGSDLIVLGGLDPITWQAHDSVFVF
2  VYRISVLELGTGLRSELPPVPGHSNGLPLFCRLVSVGSDLVVLCGLDPVTWRTSDSVFVF
3  RFGLSVYNAAMSTWHRVAFPEEEQIPLFCECVVLQDAGKILLIGGWDPETLQPTRDVYVL
4  LYGLSVYNATLDTWHRVAIP--ERIPLFCECVAIQDAGKVLLIGGWDPETLQPVRDVFVL
   **                      *   *      * ** *             * *

1  SFLT-----SKWRVGATMPGVRRSFFGCASDSDRTVLVAGGHNEEKCALTSAMVYDVSED
2  SFLT-----STWRVGKSMPGGPRSFFACASDSQRNVFVAGGHDEDKNAMMSALVYDVAED
3  EFAG-----RKWRRGAPMKES-RSFFACASVSPTKVYVAGGHDDQKNALRSAEVYDVEKD
4  DFFAGEGSGRRFRRGRPMSAA-RSFFACASVGSTKVYVAGGHDDQKNALRSAEVYDVEKD
    *        *  *  *    **** ***     * *****    *   ** ****   *

1  KWTFLPDMARERDECKAVFHAG--RFHVIGGYATEEQGQFSKTAESFDVSTWEWGPLTED
2  RWAFLPDMGRERDECTAIFHAG--KFHVIGGYSTEEQGQFSKTAESFDVTTWRWSPQGEE
3  EWSSVTPMTEGRDECQGFAVGMGLRFCVLSGYGTESQGRFRSDGEIYDPATDSWSRIDNV
4  EWSMLPPMTEGRDECHGFSMATDPGFCVLSGYGTETQGQFRSDGEIYDPITNSWSTIENV
    *       *    ****         * *  ** ** **  *        *   *    *

1  FLDDTGDTVSPP---------------TCVAG--GDLYACWGGDVMMFLNDKWQKVGQI
2  FLSS-EMTMWPP---------------ICAAGENGDLYACCRRDLMMMKDDTWYKVGNL
3  WRFPDTSPRGRTAGDFRSSS------TLWCFTDTDLQSERRWETNDDSRNLKLDLQSIQL
4  WPFPDLSPRGRTAAAAAEFPGDFRGCRLWCFIDSERQSQPHWEVEDDSMKWKVIMDTIRL
                                  *

1  PADVYNVTYVAVRPGMLIVIGNGKALAGYGEATVGYICDLSSSRWVKLETHG---GHVQA
2  PADVCNVSYVAIRRSGNLVVIG---SARYGEPSVGYNWDMSNSRWLKLETHDKYEGHVQA
3  PMTGSS-VFAGSLGGESVVMIGGKRESEGEGEGGVMMKMTTEKKMGKWSHHVHIPCDFST
4  PVTTMTSVFAGSLSGQAVAMIGG-----GGEESGTMMVKTTAEKNGGKWSHVNTPSGFSS
   *                                                        *

1  GCFLEV---- (SEQ ID NO:1)
2  GCFLEI---- (SEQ ID NO:2)
3  LPFSHASIYV (SEQ ID NO:3)
4  LPFSCSSIYV (SEQ ID NO:4)
       *
```

*FIG. 3*

```
Sb04g023200      ELIPGLPDDVAMECLARVPSRSHRRMRRVCRGWRGTVGSAEFR-RR
Os02g35530       ELIPGLPDDVAMECLARVPSRSHRAVRRVCRGWRRAAASEAFR-RR
Sb05g006950      DLIPGIPDDVAVDCLARVPHASHRAMRGVCRGWRSAASTPAFASAR
Sb05g006960      DLIPGIPDDVAVDCLARVPHASHRAMRRVCRGWRSAASTPAFASAR
GRMZM2G025783    ELIPGIPDDVAVDCLARVPHASHRAMRRVCRGWRSAAAPAFASAR
Os11g14140       ELIPGMPDDVAVDCLARVPHGAHRAMRRVCRGWRSAAATPAFAMAR
KMD3             ELIPGLPSELALECLVRVPFQFQSAMRSVCRSWRSLLSDSSFIQER
KMD4             DLIPGLPEELAIECLVRVPFQFHSSIKSVCRSWKCVISSRSFIKER
KMD1             ELIPNLPDDVARECLLRSSYQQFPVIASVCRAWNREVSLSQFLHQR
KMD2             ELIPDLPETVAYECLLRSSYKQFPLMASVCKLWQREISLSDFFRHR
                 :***.:*. :* :** * .      :  **: *.   .  *   *
```

FIG. 4

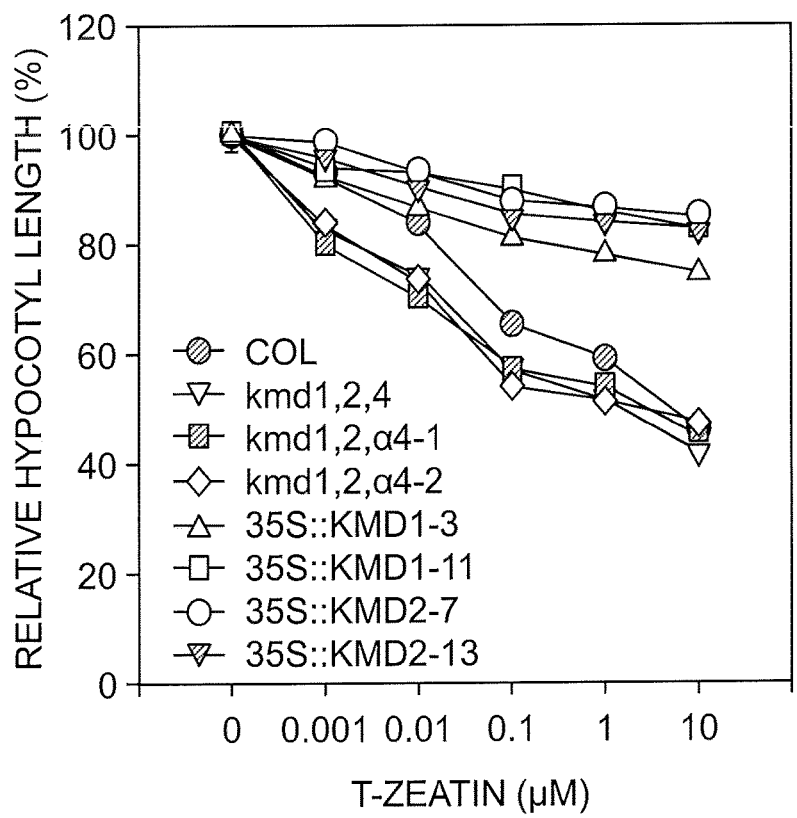

FIG. 5A

COMPOSITIONS AND METHOD FOR MODULATING THE SENSITIVITY OF PLANTS TO CYTOKININ

INTRODUCTION

This application is a U.S. National Stage Application of PCT/US2014/030953 filed Mar. 18, 2014 and claims the benefit of priority of U.S. Provisional Application No. 61/803,606, filed Mar. 20, 2013, the contents of each of which are incorporated herein by reference in their entirety.

This invention was made with government support under contract numbers 2007-35304-18323 awarded by the United States Department of Agriculture; and IOS-0618286 and IOS-1238051 awarded by the National Science Foundation. The government has certain rights in the invention.

BACKGROUND OF THE INVENTION

Cytokinins are mitogenic plant hormones that control multiple aspects of growth and development, including regulation of cell division and metabolism, stimulation of chloroplast, developmen, modulation of shoot and root development, and delay of leaf senescence (Hwang, et al. (2012) *Annu. Rev. Plant Biol.* 63:353-380; Perilli, et al. (2010) *Curr. Opin. Plant Biol.* 13(1):21-26). Cytokinin signals are transmitted through a multistep histidine-to-aspartate phosphorelay system, evolutionarily related to the two-component signaling systems of prokaryotes (Hwang, et al. (2012) supra; Schaller, et al. (2011) *Curr. Biol.* 21(9): R320-330). In *Arabidopsis*, cytokinins are perceived by the three receptors AHK2 (for *ARABIDOPSIS* HISTIDINE KINASE 2), AHK3, and AHK4, which, upon perception of the cytokinin signal, autophosphorylate a conserved His residue (Inoue, et al. (2001) *Nature* 409(6823):1060-1063; Ueguchi, et al. (2001) *Plant Cell Physiol.* 42(7):751-755). The regulatory phosphoryl group is passed from receptor to a histidine-containing phosphotransfer (AHP) protein, and from there to a type-B response regulator (ARR). Phosphorylation of the *Arabidopsis* type-B ARR proteins modulates their ability to control gene expression as the key transcription factors in the primary response pathway (Kim, et al. (2006) *Proc. Natl. Acad. Sci. USA* 103(3):814-819; Argyros, et al. (2008) supra). Among the transcriptional targets of the type-B ARRs are a second class of response regulators, the type-A ARRs, which act as negative regulators of the signal transduction pathway (To, et al. (2004) *Plant Cell* 16(3): 658-671). This model of cytokinin signal transduction has been established largely based on studies in *Arabidopsis*, but similar two-component signaling components have been identified in other plant species such as the monocot rice and the moss *Physcomitrella patens*, supporting a common pathway for the transmission of the cytokinin signal in land plants (Pils & Heyl (2009) *Plant Physiol.* 151(2):782-791; Tsai, et al. (2012) *Plant Physiol.* 158(4):1666-1684).

Control of protein stability through ubiquitin-mediated proteolysis has emerged as a central theme in plant growth and development over the past decade (Hua & Vierstra (2011) *Annu. Rev. Plant Biol.* 62:299-334). E3 ubiquitin ligases have been identified that target key signaling elements for degradation in many plant hormone signaling pathways, including those for auxin, ethylene, gibberellin, and jasmonic acid (Santner & Estelle M (2010) *Plant J.* 61(6):1029-1040). Identification of such a regulatory component for cytokinin signal transduction has not been confirmed, though several studies suggest that the ubiquitin-proteasome system plays a role in the regulation of cytokinin signaling (Kim, et al. (2012) *Plant J.* 69(6):934-945; Dharmasiri, et al. (2005) *Nature* 435(7041):441-445; Zheng, et al. (2011) *Plant Physiol.* 156(4):1878-1893; Smalle, et al. (2002) *Plant Cell* 14(1):17-32; To, et al. (2007) *Plant Cell* 19(12):3901-3914). Most significantly, the stability of the type-B response regulator ARR2 decreases in the presence of cytokinin, and a more stable mutant version of ARR2 enhances cytokinin sensitivity in various developmental processes (Kim, et al. (2012) supra).

The irreversible degradation of cytokinins, catalyzed by cytokinin oxidase, is an important mechanism by which plants modulate their cytokinin levels (Houba-Herin (1999) *Plant J.* 17:615-626; Morris, et al. (1999) *Biochem. Biophys. Res. Commun.* 255:328-333; Brugiere, et al. (2003) *Plant Physiol.* 132:1228-1240). The catabolic enzyme cytokinin oxidase (CKX) plays a major role in controlling cytokinin levels in plant tissues and methods for modulating plant development via CKX have been described (U.S. Pat. No. 8,222,483). F-box proteins have also been suggested as targets for regulating cytokinin production See US 2012/0216318. However, the use of a particular F-box from the hundreds of F-box proteins identified in plants has not been suggested.

In view of the influence of cytokinins on a wide variety of plant developmental processes, including root architecture, shoot and leaf development, and seed set, the ability to manipulate responses to cytokinin in higher plant cells, and thereby affect plant growth and productivity, is of great commercial value.

SUMMARY OF THE INVENTION

The present invention includes an expression cassette containing a polynucleotide encoding a polypeptide of SEQ ID NO:1, SEQ ID NO:2, SEQ ID NO:3, SEQ ID NO:4 or SEQ ID NO:5; and a host cell, transgenic plant (e.g., a dicot or monocot), transformed seed, and transgenic rootstock containing said expression cassette.

Methods for desensitizing a plant to endogenous cytokinin; increasing seed, embryo or cotyledon size or weight; increasing the seed yield of a plant; and increasing the size of the root or root meristem or formation of lateral or adventitious roots are also provided. In some embodiments, the expression of the polypeptide is under control of a seed-preferred, embryo-preferred promoter or root-preferred promoter.

BRIEF DESCRIPTION OF THE DRAWINGS

FIG. 3 shows an alignment of KMD1 ("1," At1g80440), KMD2 ("2," At1g15670), KMD3 ("3," At2g44130), and KMD4 ("4," At3g59940) amino acid sequences. Identical amino acid residues in the four proteins are indicated with asterisks. F-box motif sequences are boxed and the Kelch-repeat domains are underlined.

FIG. 4 shows an alignment of F-box motifs from orthologs (Sb04g023200, SEQ ID NO:6; Os02g35530, SEQ ID NO:7; Sb05g006950, SEQ ID NO:8; Sb05g006960, SEQ ID NO:9; GRM2M2G025783, SEQ ID NO:10; Os11g14140, SEQ ID NO:11) of the KMD proteins (KMD3, SEQ ID NO:12; KMD4, SEQ ID NO:13; KMD1, SEQ ID NO:14; KMD2, SEQ ID NO:15). Identities and similarities are respectively indicated with an asterisk and colon.

FIGS. 5A and 5B respectively show the effect of cytokinin on hypocotyls and root growth of Col; kmd1,2,4; kmd1,2, α,4 antisense lines, and KMD-overexpression lines (35S:: KMD1-3, 35S::KMD1-11, 35S::KMD2-7 and 35S::KMD2-13). In FIG. 5A, etiolated seedlings were grown for 4 days on the indicated concentrations of t-zeatin. Error bars are ±SEM (n≥20). In FIG. 5B, seedlings were grown on vertical plates supplemented with t-zeatin under constant light. Increase in root length from day 4 through day 7 was measured. Error bars are ±SEM (n≥18).

DETAILED DESCRIPTION OF THE INVENTION

Figure 1:
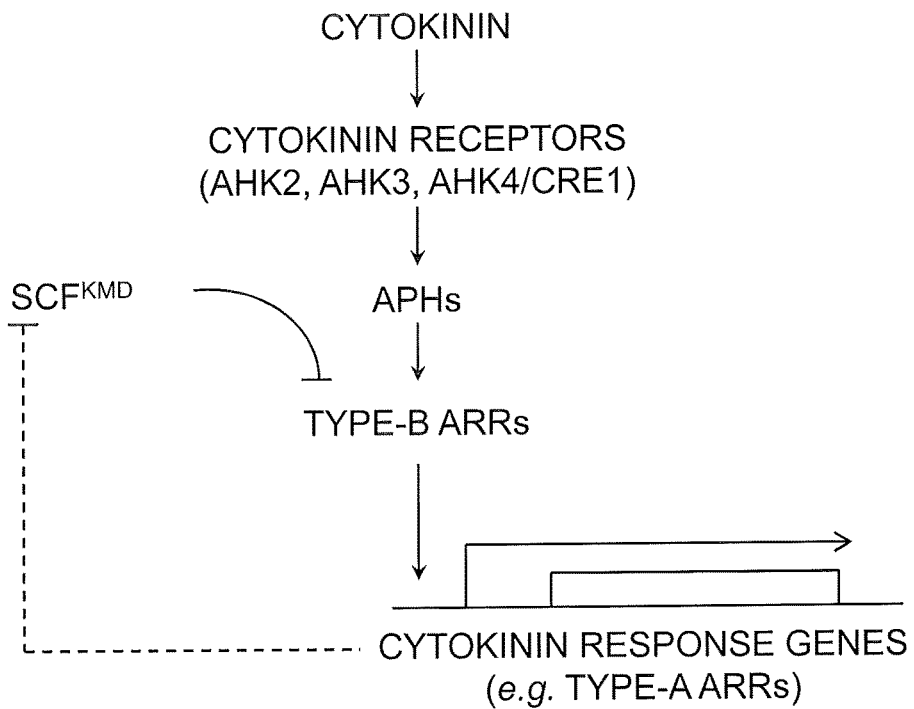
FIG. 1 depicts a model for the role of the KISS ME DEADLY (KMD) and SKP1/Cullin/F-box protein complex (SCF$^{KMD}$) in the cytokinin signaling pathway. Cytokinin acts through a signaling pathway that involves cytokinin receptors (AHKs), histidine-containing phosphotransfer proteins (AHPs), and the type-B ARR family of transcription factors. SCF$^{KMD}$ targets the type-B ARRs for degradation through the ubiquitin-proteasome pathway to reduce their transcriptional output (solid line for repression). KMD gene expression is itself under transcriptional control with the cytokinin signal inducing a decrease in KMD gene expression (dashed line for repression).

Cytokinins are plant hormones that play critical roles in growth and development. In *Arabidopsis*, the transcriptional response to cytokinin is regulated by action of the type-B response regulators (ARRs). It has now been found that a family of F-box proteins, called the KISS ME DEADLY (KMD) family, targets the type-B ARR proteins for degradation. KMD proteins form an SKP1/Cullin/F-box protein (SCF) E3 ubiquitin ligase complex and directly interact with type-B ARR proteins. Loss-of-function KMD mutants stabilize type-B ARRs and exhibit an enhanced cytokinin response. In contrast, plants with elevated KMD expression destabilize type-B ARR proteins leading to cytokinin insensitivity. These results support a model in which an $SCF^{KMD}$ complex negatively regulates cytokinin responses by controlling levels of a key family of transcription factors (FIG. 1). The cytokinin signaling pathway is conserved in plants, and homologues to KMDs exist in the monocot rice (FIG. 2), indicating the broad conservation of this regulatory mechanism for controlling the cytokinin transcriptional output.

With the identification of a role for $SCF^{KMD}$ in regulating cytokinin levels, the present invention provides compositions and methods for regulating the sensitivity of plants to cytokinin and modulating the growth and development of plants including increasing seed size and/or weight, and increasing the growth of the root system including, e.g., mass, length and/or branching.

Compositions of the invention include KMD polypeptides and polynucleotides that are involved in modulating sensitivity to cytokinin and in plant development, morphology, and physiology, as well as expression cassettes, host cells, and transgenic plants containing the same. In particular, the present invention provides for isolated polynucleotides having nucleotide sequences encoding the amino acid sequence shown in SEQ ID NO:1, SEQ ID NO:2, SEQ ID NO:3 or SEQ ID NO:4 and SEQ ID NO:5 (FIG. 3).

In certain embodiments, the invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb or 0.1 kb of nucleotide sequence that naturally flank the polynucleotide in genomic DNA of the cell from which the polynucleotide is derived.

A protein that is substantially free of cellular material includes preparations of protein having less than about 30%, 20%, 10%, 5% or 1% (by dry weight) of contaminating protein. When the protein of the invention or biologically active portion thereof is recombinantly produced, optimally culture medium represents less than about 30%, 20%, 10%, 5% or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence of the protein encoded thereby. Fragments of a polynucleotide may encode protein fragments that retain the biological activity of the native protein and hence interact with ARRs. Alternatively, fragments of a polynucleotide, which are useful as hybridization probes generally do not encode protein fragments retaining biological activity. Thus, fragments of a nucleotide sequence may range from at least about 20 nucleotides, about 50 nucleotides, about 100 nucleotides and up to a full-length polynucleotide encoding a protein of the invention.

A fragment of a KMD polynucleotide that encodes a biologically active portion of a KMD protein of the invention will encode at least 15, 25, 30, 50, 100, 150, 200, 250, 300, 350, or 400 contiguous amino acids, or up to the total number of amino acids present in a full-length KMD protein of the invention (for example, 354 amino acids, 359 amino acids, 409 amino acids, 418 amino acids and 381 amino acids for SEQ ID NO:1, 2, 3, 4 and 5, respectively). Fragments of a KMD polynucleotide that are useful as hybridization probes or PCR primers generally need not encode a biologically active portion of a KMD protein. Thus, a fragment of a KMD polynucleotide may encode a biologically active portion of a KMD protein, or it may be a fragment that can be used as a hybridization probe or PCR primer using methods disclosed below.

A biologically active portion of a KMD protein can be prepared by isolating a portion of one of the KMD polynucleotides of the invention, expressing the encoded portion of the KMD protein (e.g., by recombinant expression in vitro), and assessing the activity of the encoded portion of the KMD protein. Polynucleotides that are fragments of a KMD nucleotide sequence include at least 16, 20, 50, 75, 100, 150, 200, 250, 300, 350, 400, 450, 500, 550, 600, 650, 700, 800, 900, 1000, 1100, or 1200 nucleotides, or up to the number of nucleotides present in a full-length KMD polynucleotide disclosed herein.

"Variants" is intended to mean substantially similar sequences. For polynucleotides, a variant includes a deletion and/or addition of one or more nucleotides at one or more sites within the native polynucleotide and/or a substitution of one or more nucleotides at one or more sites in the native polynucleotide. As used herein, a "native" polynucleotide or polypeptide includes a naturally occurring nucleotide sequence or amino acid sequence, respectively. For polynucleotides, conservative variants include those sequences that, because of the degeneracy of the genetic code, encode the amino acid sequence of one of the KMD polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a KMD protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the polypeptide of SEQ ID NO: 1, 2, 3, 4 or 5 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more sites in the native protein and/or substitution of one or more amino acids at one or more sites in the native protein. Variant proteins encompassed by the present invention are biologically active, that is they continue to possess the desired biological activity of the native protein, that is, KMD activity as described herein. Such variants may result from, for example, genetic polymorphism or from human manipulation. Biologically active variants of a native KMD protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2 or even 1 amino acid residue. The upper limit of variation for an amino acid sequence of the invention which retains biological activity can be determined empirically, i.e., by testing variants in an assay for KMD activity as described elsewhere herein. A biologically active variant of a protein of the invention may differ from that protein by as much as 100 or 200 amino acids. One of skill in the art would note that conservation of functional motifs, such as the F-box motif and Kelch-repeat domain identified in FIGS. 3 and 4 is preferred.

The proteins of the invention may be altered in various ways including amino acid substitutions, deletions, truncations, and insertions. Methods for such manipulations are generally known in the art. For example, amino acid sequence variants and fragments of the KMD proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel, et al. (1987) *Methods in Enzymol.* 154:367-382; U.S. Pat. No. 4,873,192; Walker & Gaastra, eds. (1983) *Techniques in Molecular Biology* (MacMillan Publishing Company, New York). Guidance as to appropriate amino acid substitutions that do not affect biological activity of the protein of interest may be found in the model of Dayhoff, et al. (1978) *Atlas of Protein Sequence and Structure* (Natl. Biomed. Res. Found., Washington, D.C.). Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass both naturally occurring proteins as well as variations and modified forms thereof. Such variants will continue to possess the desired KMD activity. The mutations that will be made in the DNA encoding the variant must not place the sequence out of reading frame and optimally will not create complementary regions that could produce secondary mRNA structure. See, EP 0075444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assaying for KMD activity. KMD activity can be assayed in a variety of ways. For example, binding to ARR proteins or regulation of Type-B ARR degradation.

Variant polynucleotides and proteins also encompass sequences and proteins derived from a mutagenic and recombinogenic procedure such as DNA shuffling. With such a procedure, one or more different KMD sequences can be manipulated to create a new KMD polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the KMD gene of the invention and other known KMD genes to obtain a new gene coding for a protein with an improved property of interest. Strategies for such DNA shuffling are known in the art. See, for example, Stemmer (1994) *Proc. Natl. Acad. Sci. USA* 91:10747-10751; Stemmer (1994) *Nature* 370:389-391; Crameri, et al. (1997) *Nature Biotech.* 15:436-438; Moore, et al. (1997) *J. Mol. Biol.* 272:336-347; Zhang, et al.

(1997) *Proc. Natl. Acad. Sci. USA* 94:4504-4509; Crameri, et al. (1998) *Nature* 391:288-291; U.S. Pat. No. 5,605,793 and U.S. Pat. No. 5,837,458.

The polynucleotides of the invention (i.e., the KMD sequences) can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire KMD sequences or the KMD promoter sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99% or greater sequence identity. Functions of orthologs are often highly conserved among species. Thus, isolated polynucleotides that encode a KMD protein and which hybridize under stringent conditions to the KMD sequences disclosed herein, or to variants or fragments or complements thereof, are encompassed by the present invention.

Figure 2:
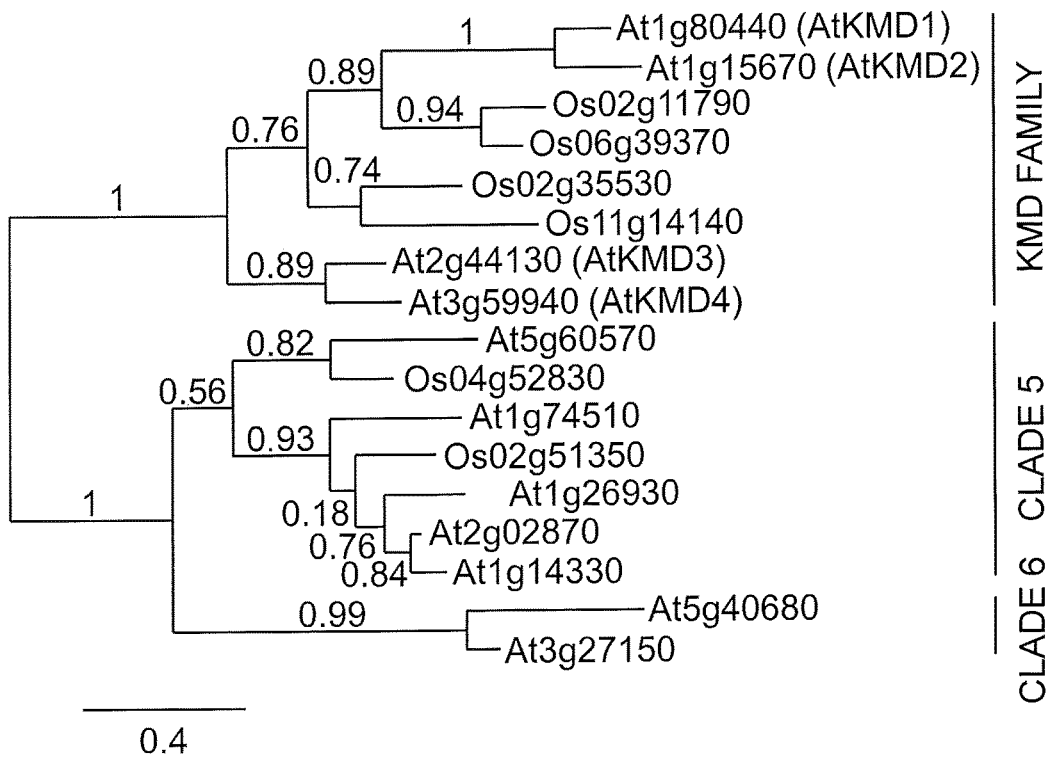
FIG. 2 shows the relationship of KMD proteins to phylogenetically closely related F-box/kelch proteins of *Arabidopsis* and rice. The phylogenetic tree was constructed using the phylogeny.fr pipeline (Dereeper (2008) *Nucl. Acids Res.* 36:W465-W469). The clades are those described in the art (Schuman, et al. (2011) *Plant Physiol.* 155:835-850).

As illustrated in FIG. 2, orthologs of the KMD proteins of this invention are present in rice. These include Gene IDs Os02g11790, Os06g39370, Os02g35530, and Os11g14140. Orthologous proteins are also present in *sorghum* (e.g. Gene ID Sb04g007310, Sb10g023140, Sb04g023200, Sb05g006950 and Sb05g006960) and maize (e.g., Gene ID GRMZM2G325650 and GRMZM2G025783). Given that the KMD proteins in *Arabidopsis*, rice, maize and *sorghum* share a conserved amino-terminal F-box motif (FIG. 4), and it has been shown that overexpression of a rice KMD protein (Os06g39370; SEQ ID NO:5) in *Arabidopsis* cytokinin insensitivity in similar fashion to the *Arabidopsis* KMD proteins, any one of the above-referenced monocot proteins can be used in the compositions and methods of this invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook, et al. (1989) *Molecular Cloning: A Laboratory Manual* (2d ed., Cold Spring Harbor Laboratory Press, Plainview, N.Y.). See also, Innis, et al., eds. (1990) *PCR Protocols: A Guide to Methods and Applications* (Academic Press, New York); Innis & Gelfand, eds. (1995) *PCR Strategies* (Academic Press, New York); and Innis & Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the KMD polynucleotides of the invention. Methods for preparation of probes for hybridization and for construction of cDNA and genomic libraries are generally known in the art and are disclosed in Sambrook, et al. (1989) *Molecular Cloning: A Laboratory Manual* (2d ed., Cold Spring Harbor Laboratory Press, Plainview, N.Y.).

For example, an entire KMD polynucleotide sequence disclosed herein, or one or more portions thereof, may be used as a probe capable of specifically hybridizing to corresponding KMD polynucleotides and messenger RNAs. To achieve specific hybridization under a variety of conditions, such probes include sequences that are unique among KMD polynucleotide sequences and are optimally at least about 10 nucleotides in length, and most optimally at least about 20 nucleotides in length. Such probes may be used to amplify corresponding KMD polynucleotides from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook, et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth & Wahl ((1984) *Anal. Biochem.* 138:267-284): $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology, Hybridization with Nucleic Acid Probes*, Part I, Chapter 2 (Elsevier, NY); and Ausubel, et al., eds. (1995) *Current Protocols in Molecular Biology*, Chapter 2 (*Greene* Publishing and Wiley-Interscience, New York). See, Sambrook, et al. (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: "reference sequence", "comparison window", "sequence identity", and, "percentage of sequence identity." As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence. As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers & Miller (1988) *CABIOS* 4:11-17; the local alignment algorithm of Smith, et al. (1981) *Adv. Appl. Math.* 2:482; the global alignment algorithm of Needleman & Wunsch (1970) *J. Mol. Biol.* 48:443-453; the search-for-local alignment method of Pearson & Lipman (1988) *Proc. Natl. Acad. Sci.* 85:2444-2448; the algorithm of Karlin & Altschul (1990) *Proc. Natl. Acad. Sci. USA* 872264, modified as in Karlin & Altschul, (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., San Diego, Calif.). Alignments using these programs can be performed using the default parameters. The CLUSTAL program is well described by Higgins, et al. (1988) *Gene* 73:237-244 (1988); Higgins, et al. (1989) *CABIOS* 5:151-153; Corpet, et al. (1988) *Nucleic Acids Res.* 16:10881-90; Huang, et al. (1992) *CABIOS* 8:155-65; and Pearson, et al. (1994) *Meth. Mol. Biol.* 24:307-331. The ALIGN program is based on the algorithm of Myers & Miller (1988) supra. A PAM120 weight residue table, a gap length penalty of 12, and a gap penalty of 4 can be used with the ALIGN program when comparing amino acid sequences. The BLAST programs of Altschul, et al. (1990) *J. Mol. Biol.* 215:403 are based on the algorithm of Karlin & Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul, et al. (1997) *Nucleic Acids Res.* 25:3389. Alternatively, PSI-BLAST (in BLAST 2.0) can be used to perform an iterated search that detects distant relationships between molecules. See, Altschul, et al. (1997) supra. When utilizing BLAST, Gapped BLAST, PSI-BLAST, the default parameters of the respective programs (e.g., BLASTN for nucleotide sequences, BLASTX for proteins) can be used.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may include additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The invention further provides plants having altered levels and/or activities of the KMD polypeptides of the invention. In some embodiments, the plants of the invention have stably incorporated into their genomes one or more of the KMD sequences of the invention.

As used herein, the term plant includes plant cells, plant protoplasts, plant cell tissue cultures from which a plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, grain and the like. As used herein, by "grain" is intended the mature seed produced by commercial growers for purposes other than growing or reproducing the species. Progeny, variants, and mutants of the regenerated plants are also included within the scope of the invention, provided that these parts comprise the introduced nucleic acid sequences.

A "subject plant" or "subject plant cell" is one in which genetic alteration, such as transformation, has been effected as to a gene of interest, or is a plant or plant cell which is descended from a plant or plant cell so altered and which comprises the alteration. A "control" or "control plant" or "control plant cell" provides a reference point for measuring changes in the subject plant or plant cell.

A control plant or control plant cell may include, for example, (a) a wild-type plant or plant cell, i.e., of the same genotype as the starting material for the genetic alteration which resulted in the subject plant or subject plant cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or subject plant cell; (d) a plant or plant cell genetically identical to the subject plant or subject plant cell but which is not exposed to conditions or stimuli that would induce expression of the gene of interest; or (e) the subject plant or subject plant cell itself, under conditions in which the gene of interest is not expressed.

In the present case, for example, in various embodiments, changes in KMD levels, sensitivity to cytokinin and/or changes in one or more traits such as flowering time, seed set, branching, senescence, stress tolerance, or root mass, could be measured by comparing a subject plant or subject plant cell to a control plant or control plant cell.

The sequences of the present invention can be introduced/expressed in a host cell such as bacteria, yeast, insect, mammalian, or optimally plant cells. It is expected that those of skill in the art are knowledgeable in the numerous systems available for the introduction of a polypeptide or a nucleotide sequence of the present invention into a host cell.

By "host cell" is meant a cell which harbors a heterologous nucleic acid sequence of the invention. Host cells may be prokaryotic cells such as *E. coli*, or eukaryotic cells such as yeast, insect, amphibian, or mammalian cells. Host cells can also be monocotyledonous or dicotyledonous plant cells.

The use of the term "polynucleotide" is not intended to limit the present invention to polynucleotides comprising DNA. Those of ordinary skill in the art will recognize that polynucleotides can include ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The KMD polynucleotide sequences of the invention can be provided in expression cassettes for expression in the organism of interest. The cassette may include 5' and 3' regulatory sequences operably linked to a KMD polynucleotide of the invention. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by "operably linked" is intended that the coding regions are in the same reading frame. The cassette may additionally contain at least one additional gene to be cotransformed into the organism. Alternatively, any additional gene(s) can be provided on multiple expression cassettes. Such an expression cassette is provided with a plurality of restriction sites and/or recombination sites for insertion of the KMD polynucleotide to be under the transcriptional regulation of the regulatory regions. The expression cassette may additionally contain selectable marker genes.

The expression cassette may include in the 5'-3' direction of transcription, a transcriptional and translational initiation region (i.e., a promoter), a KMD polynucleotide of the invention, and a transcriptional and translational termination region (i.e., termination region) functional in the host cell (i.e., the plant). The regulatory regions (i.e., promoters, transcriptional regulatory regions, and translational termination regions) and/or the KMD polynucleotide of the invention may be native/analogous to the host cell or to each other. Alternatively, the regulatory regions and/or the KMD polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

A termination region may be native with the transcriptional initiation region, may be native with the operably linked KMD polynucleotide of interest or with the KMD promoter sequences, may be native with the plant host, or may be derived from another source (i.e., foreign or heterologous) to the promoter, the KMD polynucleotide of interest, the plant host, or any combination thereof. Convenient termination regions are available from the Ti-plasmid of *A. tumefaciens*, such as the octopine synthase and nopaline synthase termination regions. See also, Guerineau, et al. (1991) *Mol. Gen. Genet.* 262:141-144; Proudfoot (1991) *Cell* 64:671-674; Sanfacon, et al. (1991) *Genes Dev.* 5:141-149; Mogen, et al. (1990) *Plant Cell* 2:1261-1272; Munroe, et al. (1990) *Gene* 91:151-158; Ballas, et al. (1989) *Nucleic Acids Res.* 17:7891-7903; and Joshi, et al. (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell & Gowri (1990) *Plant Physiol.* 92:1-11 for a discussion of host-preferred codon usage. Methods are available in the art for synthesizing plant-preferred genes. See, for example, U.S. Pat. No. 5,380,831; U.S. Pat. No. 5,436,391; and Murray, et al. (1989) *Nucleic Acids Res.* 17:477-498.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al. (1989) *Proc. Natl. Acad. Sci. USA* 86:6126-6130); potyvirus leaders, for example, TEV leader (Tobacco Etch Virus) (Gallie, et al. (1995) *Gene* 165(2):233-238), MDMV leader (Maize Dwarf Mosaic Virus) (Johnson, et al. (1986) *Virology* 154:9-20), and human immunoglobulin heavy-chain binding protein (BiP) (Macejak, et al. (1991) *Nature* 353: 90-94); untranslated leader from the coat protein mRNA of alfalfa mosaic virus (AMV RNA 4) (Jobling, et al. (1987) *Nature* 325:622-625); tobacco mosaic virus leader (TMV) (Gallie, et al. (1989) in *Molecular Biology of RNA*, ed. Cech (Liss, New York), pp. 237-256); and maize chlorotic mottle virus leader (MCMV) (Lommel, et al. (1991) *Virology* 81:382-385). See also, Della-Cioppa, et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions, may be involved.

The expression cassette can also include a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as beta-galactosidase and fluorescent proteins such as green fluorescent protein (GFP) (Su, et al. (2004) *Biotechnol Bioeng.* 85:610-9 and Fetter, et al. (2004) *Plant Cell* 16:215-28), cyan florescent protein (CYP) (Bolte, et al. (2004) *J. Cell Science* 117:943-54 and Kato, et al. (2002) *Plant Physiol.* 129:913-42), and yellow florescent protein (PHIYFP™, see, Bolte, et al. (2004) *J. Cell Science* 117: 943-54). For additional selectable markers, see generally, Yarranton (1992) *Curr. Opin. Biotech.* 3:506-511; Christopherson, et al. (1992) *Proc. Natl. Acad. Sci. USA* 89:6314-6318; Yao, et al. (1992) *Cell* 71:63-72; Reznikoff, (1992) *Mol. Microbiol.* 6:2419-2422; Barkley, et al. (1980) in *The Operon*, pp. 177-220; Hu, et al. (1987) *Cell* 48:555-566; Brown, et al. (1987) *Cell* 49:603-612; Figge, et al. (1988) *Cell* 52:713-722; Deuschle, et al. (1989) *Proc. Natl. Acad. Aci. USA* 86:5400-5404; Fuerst, et al. (1989) *Proc. Natl. Acad. Sci. USA* 86:2549-2553; Deuschle, et al. (1990) *Science* 248:480-483.

A number of promoters can be used in the practice of the invention, including the native promoter of the polynucleotide sequence of interest. The promoters can be selected based on the desired outcome. The nucleic acids can be combined with constitutive, inducible, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell, et al. (1985) *Nature* 313:810-812); rice actin (McElroy, et al. (1990) *Plant Cell* 2:163-171); ubiquitin (Christensen, et al. (1989) *Plant Mol. Biol.* 12:619-632 and Christensen, et al. (1992) *Plant Mol. Biol.* 18:675-689); PEMU (Last, et al. (1991) *Theor. Appl. Genet.* 81:581-588); MAS (Velten, et al. (1984) *EMBO J.* 3:2723-2730); ALS promoter (U.S. Pat. No. 5,659,026), and the like. Examples of other constitutive promoters are described in, for example, U.S. Pat. No. 5,608,149; U.S. Pat. No. 5,608,144; U.S. Pat. No. 5,604,121; U.S. Pat. No. 5,569,597; U.S. Pat. No. 5,466,785; U.S. Pat. No. 5,399,680; U.S. Pat. No. 5,268,463; U.S. Pat. No. 5,608,142 and U.S. Pat. No. 6,177,611.

Tissue-preferred promoters can be utilized to target enhanced KMD expression within a particular plant tissue. Tissue-preferred promoters include those disclosed by Yamamoto, et al. (1997) *Plant J.* 12(2):255-265; Kawamata, et al. (1997) *Plant Cell Physiol.* 38(7):792-803; Hansen, et al. (1997) *Mol. Gen. Genet.* 254(3):337-343; Russell, et al. (1997) *Transgenic Res.* 6(2):157-168; Rinehart, et al. (1996) *Plant Physiol.* 112(3):1331-1341; Van Camp, et al. (1996) *Plant Physiol.* 112(2):525-535; Canevascini, et al. (1996) *Plant Physiol.* 112(2):513-524; Yamamoto, et al. (1994) *Plant Cell Physiol.* 35(5):773-778; Lam, (1994) *Results Probl. Cell Differ.* 20:181-196; Orozco, et al. (1993) *Plant Mol. Biol.* 23(6):1129-1138; Matsuoka, et al. (1993) *Proc Natl. Acad. Sci. USA* 90(20):9586-9590; and Guevara-Garcia, et al. (1993) *Plant J.* 4(3):495-505. Such promoters can be modified, if necessary, for weak expression. See, also, US 2003/0074698. Promoters active in maternal plant tissues, such as female florets, ovaries, aleurone, pedicel, and pedicel-forming region, either pre-pollination or upon pollination, may be of particular interest.

Leaf-preferred promoters are known in the art. See, for example, Yamamoto, et al. (1997) *Plant J.* 12(2):255-265; Kwon, et al. (1994) *Plant Physiol.* 105:357-67; Yamamoto, et al. (1994) *Plant Cell Physiol.* 35(5):773-778; Gotor, et al. (1993) *Plant J.* 3:509-18; Orozco, et al. (1993) *Plant Mol. Biol.* 23(6):1129-1138; Baszczynski, et al. (1988) *Nucl. Acid Res.* 16:4732; Mitra, et al. (1994) *Plant Mol. Biol.* 26:35-93; Kayaya, et al. (1995) *Mol. Gen. Genet.* 248:668-674; and Matsuoka, et al. (1993) *Proc. Natl. Acad. Sci. USA* 90(20):9586-9590. Senescence regulated promoters are also of use, such as SAM22 (Crowell, et al. (1992) *Plant Mol. Biol.* 18:459-466).

Root-preferred or root-specific promoters are known and can be selected from the many available from the literature or isolated de novo from various compatible species. See, for example, Hire, et al. (1992) *Plant Mol.* Biol. 20(2):207-218 (soybean root-specific glutamine synthetase gene); Keller & Baumgartner (1991) *Plant Cell* 3(10):1051-1061 (root-specific control element in the GRP 1.8 gene of French bean); Sanger, et al. (1990) *Plant Mol. Biol.* 14(3):433-443 (root-specific promoter of the mannopine synthase (MAS) gene of *Agrobacterium tumefaciens*); and Miao, et al. (1991) *Plant Cell* 3(1):11-22 (full-length cDNA clone encoding cytosolic glutamine synthetase (GS), which is expressed in roots and root nodules of soybean). See also, Bogusz, et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a beta-glucuronidase reporter gene and introduced into both the nonlegume *Nicotiana tabacum* and the legume *Lotus corniculatus*, and in both instances root-specific promoter activity was preserved. Promoters of the highly expressed rolC and rolD root-inducing genes of *Agrobacterium rhizogenes* have also been described (see, Leach & Aoyagi (1991) *Plant* Science (Limerick) 79(1):69-76). Additional root-preferred promoters include the VfENOD-GRP3 gene promoter (Kuster, et al. (1995) *Plant Mol. Biol.* 29(4):759-772); rolB promoter (Capana, et al. (1994) *Plant Mol. Biol.* 25(4):681-691; and the CRWAQ81 root-preferred promoter with the ADH first intron (U.S. Ser. No. 10/961,629). See also, U.S. Pat. No. 5,837,876; U.S. Pat. No. 5,750,386; U.S. Pat. No. 5,633,363; U.S. Pat. No. 5,459,252; U.S. Pat. No. 5,401,836; U.S. Pat. No. 5,110,732 and U.S. Pat. No. 5,023,179.

Seed-preferred promoters include those promoters active during seed development, such as those expressed preferentially in female reproductive tissues, and those regulating seed storage proteins, as well as those promoters active during seed germination. See, Thompson, et al. (1989) *BioEssays* 10:108. Such seed-preferred promoters include, but are not limited to, maize zag2.1 promoter, (GENBANK X80206); maize Zap promoter, also known as ZmMADS (US 2004/0025206); maize eep1 promoter (US 2004/0237147); maize lec1 promoter (U.S. Ser. No. 09/718,754); maize F3.7 promoter (Baszczynski, et al. (1997) *Maydica* 42:189-201; maize tb1 promoter (Hubbarda, et al. (2002) *Genetics* 162:1927-1935); maize Zm40 promoter (U.S. Pat. No. 6,403,862 and WO 01/21783); milps (myo-inositol-1-phosphate synthase) (see, WO 00/11177 and U.S. Pat. No. 6,225,529); and a BETL (basal endosperm transfer layer) promoter, for example, see, U.S. Pat. No. 7,119,251. Several gamma-zein promoters are known to drive endosperm-specific expression. Globulin-1 (Glob-1) is a representative embryo-specific promoter. For dicots, seed-specific promoters include, but are not limited to, bean beta-phaseolin, napin, beta-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, globulin 1, etc. See also, WO 00/12733 and U.S. Pat. No. 6,528,704, where seed-preferred promoters from end1 and end2 genes are disclosed. Additional embryo-specific promoters are disclosed in Sato, et al. (1996) *Proc. Natl. Acad. Sci.* 93:8117-8122; Nakase, et al. (1997) *Plant J.* 12:235-46; and Postma-Haarsma, et al. (1999) *Plant Mol. Biol.* 39:257-71. Additional endosperm-specific promoters are disclosed in Albani, et al. (1984) *EMBO J.* 3:1405-15; Albani, et al. (1999) *Theor. Appl. Gen.* 98:1253-62; Albani, et al. (1993) *Plant J.* 4:343-55; Mena, et al. (1998) *Plant J.* 116:53-62, and Wu, et al. (1998) *Plant Cell Physiol.* 39:885-889.

Shoot-preferred promoters include shoot meristem-preferred promoters such as promoters disclosed in Weigal, et al. (1992) *Cell* 69:843-859; Accession Number AJ131822; Accession Number Z71981; Accession Number AF049870 and shoot-preferred promoters disclosed in McAvoy, et al. (2003) *Acta Hort.* (ISHS) 625:379-385.

Dividing cell or meristematic tissue-preferred promoters have been disclosed in Ito, et al. (1994) *Plant Mol. Biol.* 24:863-878; Reyad, et al. (1995) *Mol. Gen. Genet.* 248:703-711; Shaul, et al. (1996) *Proc. Natl. Acad. Sci.* 93:4868-4872; Ito, et al. (1997) *Plant J.* 11:983-992.

Inflorescence-preferred promoters include the promoter of chalcone synthase (Van der Meer, et al. (1990) *Plant Mol. Biol.* 15:95-109), LAT52 (Twell, et al. (1989) *Mol. Gen. Genet.* 217:240-245), pollen-specific genes (Albani et al (1990) *Plant Mol. Biol.* 15:605), Zm13 (Buerrero, et al. (1993) *Mol. Gen. Genet.* 224:161-168), maize pollen-specific gene (Hamilton, et al. (1992) *Plant Mol. Biol.* 18:211-218), sunflower pollen expressed gene (Baltz, et al. (1992) *Plant J.* 2:713-721), *B. napus* pollen specific genes (Arnoldo, et al. (1992) *J. Cell. Biochem.* Abstract Number Y101204). In some embodiments, the promoter drives transgene expression in specified areas of the rice panicle. Promoters of use in this embodiment of the invention include, but are not limited to, the OsCKX2 promoter, which drives expression in the aerial stems (culms), inflorescence meristems, and flowers at the location where cytokinin levels have already been found to play a key role in panicle development and grain yield (Ashikari, et al. (2005) *Science* 309:741-745); the OsLAX1 promoter, which drives expression in the regions that give rise to new axillary meristems for panicle branches and lateral spikelets (Komatsu, et al. (2001) *Dev. Biol.* 231:364-373); Komatsu, et al. (2003) *Proc. Natl. Acad. Sci. USA* 100:11765-11770); and the OsFZP promoter, which drives expression in the more restricted regions of just the spikelet meristems (Komatsu, et al. (2003) *Development* 130:3841-3850).

Stress inducible promoters include salt/water stress-inducible promoters such as P5CS (Zang, et al. (1997) *Plant Sci.* 129:81-89); cold-inducible promoters, such as cor15a (Hajela, et al. (1990) *Plant Physiol.* 93:1246-1252), cor15b (Wlihelm, et al. (1993) *Plant Mol. Biol.* 23:1073-1077), wsc120 (Ouellet, et al. (1998) *FEBS Lett.* 423:324-328), ci7 (Kirch, et al. (1997) *Plant Mol. Biol.* 33:897-909), ci21A (Schneider, et al. (1997) *Plant Physiol.* 113:335-45); drought-inducible promoters, such as, Trg-31 (Chaudhary, et al. (1996) *Plant Mol. Biol.* 30:1247-57), rd29 (Kasuga, et al. (1999) *Nature Biotech.* 18:287-291); osmotic inducible promoters, such as, Rab17 (Vilardell, et al. (1991) *Plant Mol. Biol.* 17:985-93) and osmotin (Raghothama, et al. (1993) *Plant Mol. Biol.* 23:1117-28); and heat inducible promoters, such as heat shock proteins (Barros, et al. (1992) *Plant Mol.* 19:665-75; Marrs, et al. (1993) *Dev. Genet.* 14:27-41), and smHSP (Waters, et al. (1996) *J. Exper. Bot.* 47:325-338). Other stress-inducible promoters include rip2 (U.S. Pat. No. 5,332,808 and US 2003/0217393) and rd29a (Yamaguchi-Shinozaki, et al. (1993) *Mol. Gen. Genet.* 236:331-334).

In accordance with this invention, a KMD polypeptide or polynucleotide encoding the same is introduced into a host cell (i.e., a plant). "Introducing" or "introduced" is intended to mean presenting to the plant the polynucleotide or polypeptide in such a manner that the sequence gains access to the interior of a cell. This invention does not depend on a particular method for introducing a sequence into the host cell, only that the polynucleotide or polypeptides gains access to the interior of at least one cell of the host. Methods for introducing polynucleotide or polypeptides into host cells (i.e., plants) are known in the art and include, but are not limited to, stable transformation methods, transient transformation methods, and virus-mediated methods.

"Stable transformation" is intended to mean that the nucleotide construct introduced into a host (i.e., a plant) integrates into the genome of the plant and is capable of being inherited by the progeny thereof. "Transient transformation" is intended to mean that a polynucleotide is introduced into the host (i.e., a plant) and expressed temporally or a polypeptide is introduced into a host (i.e., a plant).

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway, et al. (1986) *Biotechniques* 4:320-334), electroporation (Riggs, et al. (1986) *Proc. Natl. Acad. Sci. USA* 83:5602-5606, *Agrobacterium*-mediated transformation (U.S. Pat. No. 5,563,055; U.S. Pat. No. 5,981,840), direct gene transfer (Paszkowski, et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; U.S. Pat. No. 5,932,782; Tomes, et al. (1995) in *Plant Cell, Tissue, and Organ Culture: Fundamental Methods*, ed. Gamborg and Phillips (Springer-Verlag, Berlin); McCabe, et al. (1988) *Biotechnology* 6:923-926); and Led transformation (WO 00/28058). Also see, Weissinger, et al. (1988) *Ann. Rev. Genet.* 22:421-477; Sanford, et al. (1987) *Partic. Sci. Technol.* 5:27-37 (onion); Christou, et al. (1988) *Plant Physiol.* 87:671-674 (soybean); McCabe, et al. (1988) *Bio/Technology* 6:923-926 (soybean); Finer & McMullen, (1991) *In Vitro Cell Dev. Biol.* 27P:175-182 (soybean); Singh, et al. (1998) *Theor. Appl. Genet.* 96:319-324 (soybean); *Datta*, et al. (1990) *Bio/Technology* 8:736-740 (rice); Klein, et al. (1988) *Proc. Natl. Acad. Sci. USA* 85:4305-4309 (maize); Klein, et al. (1988) *Bio/Technology* 6:559-563 (maize); Klein, et al. (1988) *Plant Physiol.* 91:440-444 (maize); Fromm, et al. (1990) *Bio/Technology* 8:833-839 (maize); U.S. Pat. No. 5,736,369 (cereals); Bytebier, et al. (1987) *Proc. Natl. Acad. Sci. USA* 84:5345-5349 (Liliaceae); De Wet, et al. (1985) in The Experimental Manipulation of Ovule Tissues, ed. Chapman, et al. (Longman, NY), pp. 197-209 (pollen); Kaeppler, et al. (1990) *Plant Cell Reports* 9:415-418 and Kaeppler, et al. (1992) *Theor. Appl. Genet.* 84:560-566 (whisker-mediated transformation); D'Halluin, et al. (1992) *Plant Cell* 4:1495-1505 (electroporation); Li, et al. (1993) *Plant Cell Rep.* 12:250-255 and Christou & Ford (1995) *Ann. Bot.* 75:407-413 (rice); and Osjoda, et al. (1996) *Nature Biotech.* 14:745-750 (maize via *A. tumefaciens*).

In specific embodiments, the KMD sequences of the invention can be provided to a plant using a variety of transient transformation methods. Such transient transformation methods include, but are not limited to, the introduction of the KMD protein or variants or fragments thereof directly into the plant, or the introduction of a KMD transcript into the plant. Such methods include, for example, microinjection or particle bombardment. See, for example, Crossway, et al. (1986) *Mol. Gen. Genet.* 202:179-185; Nomura, et al. (1986) *Plant Sci.* 44:53-58; Hepler, et al. (1994) *Proc. Natl. Acad. Sci.* 91: 2176-2180 and Hush, et al. (1994) *J. Cell Sci.* 107:775-784. Alternatively, the KMD polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use particles coated with polyethylimine.

In certain embodiments, the polynucleotide of the invention may be introduced into plants by contacting plants with a virus or viral nucleic acids. Generally, such methods involve incorporating an expression construct of the invention within a viral DNA or RNA molecule. It is recognized that the a KMD sequence of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. No. 5,889,191, U.S. Pat. No. 5,889,190, U.S. Pat. No. 5,866,785, U.S. Pat. No. 5,589,367, U.S. Pat. No. 5,316,931 and Porta, et al. (1996) *Mol. Biotech.* 5:209-221.

Methods are known in the art for the targeted insertion of a polynucleotide at a specific location in the plant genome. In one embodiment, the insertion of the polynucleotide at a desired genomic location is achieved using a site-specific recombination system. See, for example, WO 99/25821, WO 99/25854, WO 99/25840, WO 99/25855, and WO 99/25853; also, U.S. Pat. Nos. 6,552,248, 6,624,297, 6,573,425, 6,455,315 and 6,458,594. Briefly, the polynucleotide of the invention can be contained in a transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional methods. See, for example, McCormick, et al. (1986) *Plant Cell Rep.* 5:81-84. These plants may then be grown, and either pollinated with the same transformed strain or different strains, and the resulting progeny having appropriate expression of the desired phenotypic characteristic identified. Two or more generations may be grown to ensure that expression of the desired phenotypic characteristic is stably maintained and inherited, and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into its genome.

Pedigree breeding starts with the crossing of two genotypes, such as an elite line of interest and one other line having one or more desirable characteristics (e.g., having stably incorporated a polynucleotide of the invention, having a modulated activity and/or level of the polypeptide of the invention, etc.) which complements the elite line of interest. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection are practiced: F1->F2; F2->F3; F3->F4; F4->F5, etc. After a sufficient amount of inbreeding, successive filial generations will serve to increase seed of the developed inbred. Preferably, the inbred line includes homozygous alleles at about 95% or more of its loci.

Backcrossing can be used to transfer one or more specifically desirable traits from one line, the donor parent, to an inbred called the recurrent parent, which has overall good agronomic characteristics yet lacks that desirable trait or traits. Backcrossing may be used in combination with pedigree breeding to modify an elite line of interest, and a hybrid is made using the modified elite line. However, the same procedure can be used to move the progeny toward the genotype of the recurrent parent but at the same time retain many components of the non-recurrent parent, by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

The present invention may be used for transformation of any plant species, including, but not limited to, monocots and dicots. Examples of plant species of interest include, but are not limited to, corn or maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, grasses and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum*. Turfgrasses include, but are not limited to: annual bluegrass (*Poa annua*); annual ryegrass (*Lolium multiflorum*); Canada bluegrass (*Poa compressa*); Chewings fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithii*); Bermuda grass (*Cynodon* spp.); St. Augustine grass (*Stenotophrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue grama (*Bouteloua gracilis*); buffalo grass (*Buchloe dactyloids*); and sideoats grama (*Bouteloua curtipendula*).

In specific embodiments, plants of the present invention are crop plants (for example, corn (maize), alfalfa, sunflower, *Brassica*, soybean, cotton, safflower, peanut, sorghum, wheat, millet, tobacco, etc.).

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Typically, an intermediate host cell will be used in the practice of this invention to increase the copy number of the cloning vector. With an increased copy number, the vector containing the nucleic acid of interest can be isolated in significant quantities for introduction into the desired plant cells. In one embodiment, plant promoters that do not cause expression of the polypeptide in bacteria are employed.

Prokaryotes most frequently are represented by various strains of *E. coli*; however, other microbial strains may also be used. Commonly used prokaryotic control sequences, which are defined herein to include promoters for transcription initiation, optionally with an operator, along with ribosome binding sequences, include such commonly used promoters as the beta lactamase (penicillinase) and lactose (lac) promoter systems (Chang, et al. (1977) *Nature* 198:1056), the tryptophan (trp) promoter system (Goeddel, et al. (1980) *Nucleic Acids Res.* 8:4057) and the lambda derived PL promoter and N-gene ribosome binding site (Shimatake, et al. (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al. (1983) *Gene* 22:229-235); Mosbach, et al. (1983) *Nature* 302:543-545).

The sequences of the present invention can also be ligated to various expression vectors for use in transfecting cell cultures of, for instance, mammalian, insect, or plant origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

In certain embodiments, the polynucleotides of the present invention can be stacked with any combination of other polynucleotide sequences of interest in order to create a plant with a desired phenotype with respect to one or more traits. The combinations generated may include multiple copies of any one or more of the polynucleotides of interest.

These stacked combinations can be created by any method including, but not limited to, cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of a polynucleotide of interest. This may be combined with any combination of other suppression cassettes or overexpression cassettes to generate the desired combination of traits in the plant.

A method for modulating the level and/or activity of a KMD polypeptide in a plant is also provided. In general, level and/or activity is increased or decreased by at least 1%, 5%, 10%, 20%, 30%, 40%, 50%, 60%, 70%, 80% or 90% relative to a native control plant, plant part, or cell which did not have the sequence of the invention introduced. Modulation in the present invention may occur during and/or subsequent to growth of the plant to the desired stage of development.

A variety of methods can be employed to assay for a modulation in the level and/or activity of a KMD polypeptide. For instance, the expression level of the KMD polypeptide may be measured directly, for example, by assaying for the level of the KMD polypeptide in the plant (i.e., western or northern blot analysis), or indirectly, for example, by assaying ARR protein degradation. Methods for measuring the KMD activity are described elsewhere herein. In specific embodiments, the level and/or activity of a KMD polypeptide is modulated in vegetative tissue, in reproductive tissue, or in both vegetative and reproductive tissue. In certain embodiments, plants with an increase in KMD expression and/or activity are screened and selected for having an increase in seed and/or root development or growth.

In one embodiment, the level and/or activity of a KMD polypeptide is modulated by introducing the polypeptide or the polynucleotide of the invention into the plant. Subsequently, a plant having the introduced sequence of the invention is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate the concentration and/or activity of the KMD polypeptide in the plant. Plant forming conditions are well known in the art and discussed briefly elsewhere herein.

Methods are provided to increase the level and/or activity of a KMD polypeptide of the invention in a plant. Such increase in the level and/or activity of a KMD polypeptide of the invention can be achieved by providing to the plant a KMD polypeptide. The KMD polypeptide can be provided by introducing a KMD polypeptide into the plant, introducing into the plant a polynucleotide molecule encoding a KMD polypeptide, or by modifying a genomic locus encoding the KMD polypeptide of the invention (e.g., replacing the promoter with a constitutive promoter or promoter that provides elevated expression of KMD).

As discussed elsewhere herein, many methods are known in the art for providing a polypeptide to a plant including, but not limited to, direct introduction of the polypeptide into the plant, and introducing into the plant (transiently or stably) a polynucleotide construct encoding a polypeptide having KMD activity. It is also recognized that the methods of the invention may employ a polynucleotide that is not capable of directing, in the transformed plant, the expression of a protein or an RNA. Thus, the level and/or activity of a KMD polypeptide may be increased by altering the gene encoding the KMD polypeptide or by altering or affecting its promoter. See, U.S. Pat. No. 5,565,350 and PCT/US93/03868.

Therefore, mutagenized plants that carry mutations in KMD genes, where the mutations increase expression of the KMD gene, are provided.

As demonstrated herein, the overexpression of a KMD protein resulted in cytokinin insensitivity. Therefore, this invention, also provides a method for decreasing the sensitivity or desensitizing a plant to endogenous cytokinin by transgenically overexpressing a KMD protein in a plant. As used herein a "cytokinin" refers to a class of plant-specific hormones that play a central role during the cell cycle and influence numerous developmental programs. Cytokinins include an $N^6$-substituted purine derivative. Representative cytokinins include isopentenyladenine ($N^6$(Delta$^2$-isopentenyl)adenine (hereinafter, iP), zeatin (6-(4-hydroxy-3methyl-but-trans-2-enylamino) purine) (hereinafter, Z), and dihydrozeatin (DZ). The free bases and their ribosides (iPR, ZR, and DZR) are believed to be the active compounds. Additional cytokinins are known. See, for example, U.S. Pat. No. 5,211,738. Decreasing the sensitivity of a plant to cytokinin includes any decrease in a response to endogenous cytokinin in the plant including alterations in seed and/or root development.

Accordingly, the invention also provides a method for modulating root development in a plant. By "modulating root development" is intended any alteration in the development of the plant root when compared to a control plant. Root development is altered by introducing into a plant of interest a polynucleotide sequence encoding a KMD polypeptide and expressing the KMD polypeptide, thereby modifying root development. In one embodiment of this method, the KMD expression construct introduced into the plant is stably incorporated into the genome of the plant. Transgenic expression of KMD polypeptide can result in one or more alterations to root development, including, but not limited to, larger root meristems, increased root growth, enhanced radial expansion, an enhanced vasculature system, increased root branching, more lateral and/or adventitious roots, and/or an increase in fresh root weight when compared to a control plant.

As used herein, "root growth" encompasses all aspects of growth of the different parts that make up the root system at different stages of its development in both monocotyledonous and dicotyledonous plants. It is to be understood that enhanced root growth can result from enhanced growth of one or more of its parts including the primary root, lateral roots, adventitious roots, etc. Methods of measuring such developmental alterations in the root system are known in the art. See, for example, US 2003/0074698 and Werner, et al. (2001) Proc. Natl. Acad. Sci. USA 18:10487-10492.

As discussed above, one of skill will recognize the appropriate promoter to use to modulate root development in the plant. Exemplary promoters for this embodiment include constitutive promoters and root-preferred promoters. Exemplary root-preferred promoters have been disclosed elsewhere herein.

Stimulating root growth and increasing root mass by transgenic expression of a KMD polypeptide also finds use in improving the standability of a plant. The term "resistance to lodging" or "standability" refers to the ability of a plant to fix itself to the soil. For plants with an erect or semi-erect growth habit, this term also refers to the ability to maintain an upright position under adverse conditions, such as adverse environments. This trait relates to the size, depth and morphology of the root system. In addition, stimulating root growth and increasing root mass by transgenic expression of a KMD polypeptide also finds use in promoting in vitro propagation of explants.

Furthermore, higher root biomass production due to transgenic expression of a KMD polypeptide has a direct effect on the yield and an indirect effect on production of compounds produced by root cells or transgenic root cells or cell cultures of said transgenic root cells. One example of an interesting compound produced in root cultures is shikonin, the yield of which can be advantageously enhanced by said methods. Moreover, higher root biomass production resulting from transgenic expression of a KMD polypeptide may also impact the plant's assimilation of water and/or nutrients, favorably impacting yield of vegetative and/or reproductive tissues, including seed. Further, improved root structure may result in increased tolerance to drought, or improved nitrogen use efficiency, or improved disease resistance, or improved insect resistance, particularly when combined with an insecticidal trait. Such characteristics may be apparent at various points throughout the plant life cycle, affecting, for example, flowering, early seed development, and/or senescence. Modified plants may be more productive with current fertilizer application rates, or may maintain their productivity even under significantly reduced fertilizer input or on less fertile soils. Increased nitrogen use efficiency can result from enhanced uptake and assimilation of nitrogen fertilizer and/or the subsequent remobilization and reutilization of accumulated nitrogen reserves, enhancing yield. Improving nitrogen use efficiency in maize would increase corn harvestable yield per unit of input nitrogen, both in developing nations where access to nitrogen fertilizer is limited and in developed nations where the level of nitrogen use is high. Nitrogen utilization improvement also allows decreases in on-farm input costs, reduces dependence on non-renewable energy sources required for synthetic nitrogen fertilizer production, and decreases the environmental impact of nitrogen fertilizer manufacturing and its agricultural use.

Methods are also provided for modulating shoot and leaf development in a plant. By "modulating shoot and/or leaf development" is intended any alteration in the development of the plant shoot and/or leaf. Such alterations in shoot and/or leaf development include, but are not limited to, alterations in shoot meristem development, in leaf number, leaf size, leaf and stem vasculature, internode length, and leaf senescence. As used herein, "leaf development" and "shoot development" encompass all aspects of growth of the different parts that make up the leaf system and the shoot system, respectively, at different stages of their development, both in monocotyledonous and dicotyledonous plants. Methods for measuring such developmental alterations in the shoot and leaf system are known in the art. See, for example, Werner, et al. (2001) supra and US 2003/0074698.

The method for modulating shoot and/or leaf development in a plant includes introducing into a plant of interest a polynucleotide sequence encoding a KMD polypeptide (e.g., via an expression construct) and expressing the KMD polypeptide, thereby modifying shoot and/or leaf development. In certain embodiments, the KMD expression construct introduced into the plant is stably incorporated into the genome of the plant. As discussed above, one of skill will recognize the appropriate promoter to use to modulate shoot and leaf development of the plant. Exemplary promoters for this embodiment include constitutive promoters, shoot-preferred promoters, shoot meristem-preferred promoters, and leaf-preferred promoters. Exemplary promoters have been disclosed elsewhere herein.

Methods for modulating reproductive tissue development are also provided. In one embodiment, methods are provided to modulate floral development in a plant. By "modulating floral development" is intended any alteration in a structure of a plant's reproductive tissue as compared to a control plant in which the activity or level of the KMD polypeptide has not been modulated. "Modulating floral development" further includes any alteration in the timing of the development of a plant's reproductive tissue (i.e., a delayed or a accelerated timing of floral development) when compared to a control plant. Macroscopic alterations may include changes in size, shape, number, or location of reproductive organs, the developmental time period over which these structures form, and/or the ability to maintain or proceed through the flowering process in times of environmental stress. Microscopic alterations may include changes to the types or shapes of cells that make up the reproductive organs.

In specific methods, floral development is modulated by transgenic expression of a KMD polypeptide. An increase in KMD activity can result in one or more alterations in floral development, including, but not limited to, retarded flowering, reduced number of flowers, partial male sterility, and reduced seed set, when compared to a control plant. Inducing delayed flowering or inhibiting flowering can be used to enhance yield in forage crops such as alfalfa. Methods for measuring such developmental alterations in floral development are known in the art. See, for example, Mouradov, et al. (2002) *Plant Cell* S11-S130.

As discussed above, one of skill will recognize the appropriate promoter to use to modulate floral development of the plant. Exemplary promoters for this embodiment include constitutive promoters, inducible promoters, shoot-preferred promoters, and inflorescence-preferred promoters.

Methods are also provided for the use of a KMD expression construct to increase seed size and/or weight. The method includes transgenically expressing a KMD polypeptide in a plant or plant part, such as the seed, to increase in seed size and/or weight including the size or weight of one or more seed parts including, for example, the embryo, endosperm, seed coat, aleurone, and/or cotyledon. An increase in seed size and/or weight is intended to include an increase in at least one of weight of seeds, number of filled seeds or harvest index, relative to a corresponding wild type plant. As discussed above, one of skill will recognize an appropriate promoter to use to increase seed size and/or seed weight. Exemplary promoters of this embodiment include constitutive promoters, inducible promoters, seed-preferred promoters, embryo-preferred promoters, endosperm-preferred promoters, and promoters active in female reproductive tissues immediately pre- and post-pollination.

It is further recognized that increasing seed size and/or weight can also be accompanied by an increase in the speed of growth of seedlings or an increase in early vigor. As used herein, the term "early vigor" refers to the ability of a plant to grow rapidly during early development, and relates to the successful establishment, after germination, of a well-developed root system and a well-developed photosynthetic apparatus. In addition, an increase in seed size and/or weight can result in an increase in plant yield when compared to a control.

Accordingly, the present invention further provides plants having an increased seed weight and/or seed size when compared to a control plant. In other embodiments, plants having an increased vigor and plant yield are also provided. In some embodiments, the plant of the invention transgenically expresses a KMD polypeptide and has an increased seed weight and/or seed size.

Transgenic expression of a KMD polypeptide can also be used to modify the tolerance of a plant to abiotic stress. Increases in the growth of seedlings or early vigor are often associated with increase in stress tolerance. For example, faster development of seedlings, including the root system of seedlings upon germination, is critical for survival, particularly under adverse conditions such as drought or low temperatures. Promoters that can be used in this method are described elsewhere herein and include constitutive, root-preferred, or stress-induced promoters. Accordingly, in one method of the invention, a plant's tolerance to stress is increased or maintained when compared to a control plant by transgenic expression of a KMD polypeptide in one or more parts of the plant. In some methods, a KMD polynucleotide is provided by introducing into the plant an expression cassette harboring a KMD polynucleotide, expressing the KMD polynucleotide, and thereby increasing the plant's tolerance to stress. In certain embodiments, the KMD polynucleotide introduced into the plant is stably incorporated into the genome of the plant.

Methods are also provided to increase or maintain seed set during abiotic stress episodes. During periods of stress (i.e., drought, salt, heavy metals, temperature extremes, etc.) embryo development is often aborted. In maize, halted embryo development results in aborted kernels on the ear. Preventing this kernel loss will maintain yield. Accordingly, methods are provided to increase the stress resistance in a plant (for example, by transgenic expression of a KMD polypeptide in an early developing embryo or endosperm). Transgenic expression of a KMD polypeptide in appropriate tissues can also modulate floral development during periods of stress, and thus methods are provided to maintain or improve the flowering process in plants under stress.

Methods for modulating pathogen resistance in a plant are provided. Plant pathogens can produce cytokinins (Mills, et al. (1978) *Physiol. Plant Pathol.* 13:73-80 and Angra, et al. (1990) *Mycopathologia* 109:177-182). Accordingly, desensitization of a plant or plant part to cytokinin can increase the plant's resistance to the pathogen. See, for example, Bilyeu, et al. (2001) *Plant Physiol.* 125:378-386. Thus, compositions and methods for inducing resistance in a plant or plant part are provided. In specific embodiments, the KMD polypeptide is provided to the developing seed and thereby increases the pathogen resistance of the seed. Accordingly, the compositions and methods are also useful in protecting plants against fungal pathogens, viruses, nematodes, insects and the like.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen are minimized or lessened.

In addition to desensitizing a plant to cytokinin, some embodiments also pertain to increasing the sensitivity of a plant to cytokinin. In accordance with this embodiment, the level and/or activity of a KMD polypeptide is decreased. For example, inhibitory molecules can be used to target the interface between KMD and SCF or KMD and ARR proteins. Such molecules can be identified in conventional screen assays. By way of illustration, small molecule inhibitors specific to the binding interface between SCF-Skp2 (S-phase kinase-associated protein 2; F-box protein) and p27 (a tumor suppressor) have been identified (compounds C1, C2, C16 and C20). See Wu, et al. (2012) *Chem. Biol.* 19:1515-24.

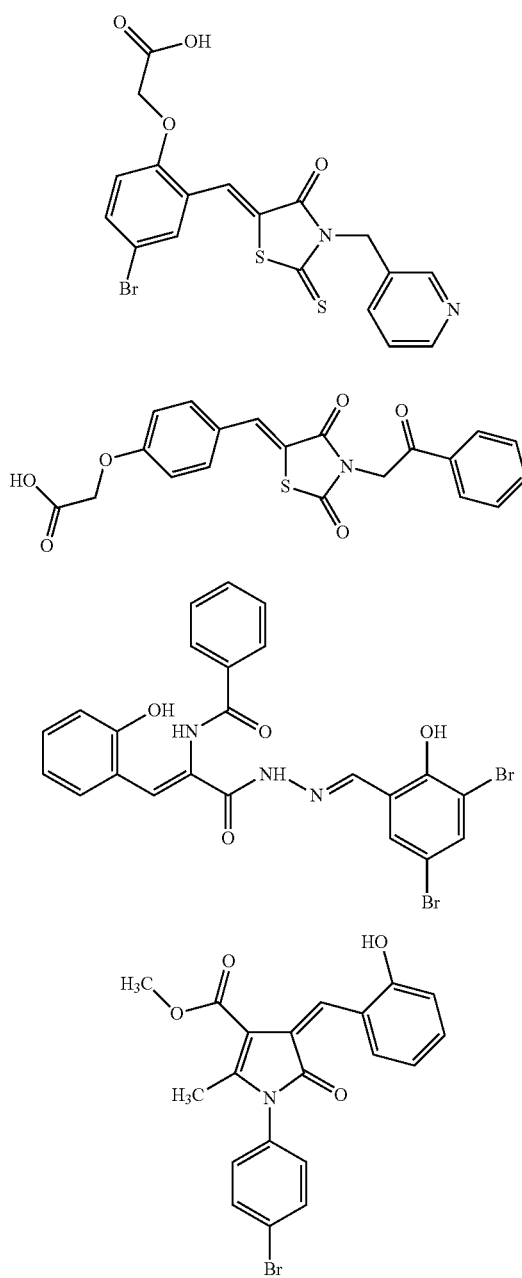

Compounds that sensitize a plant to cytokinin find application in application in increasing shoot development and yields of fruit, vegetables, and grain.

The invention will be further described in the following examples, which do not limit the scope of the invention described in the claims.

EXAMPLE 1

Materials and Methods

Plant Materials and Growth Conditions. *Arabidopsis thaliana* Columbia (Col-0) ecotype was the parent strain for mutants and transgenic lines. The kmd1-1 (SALK_008497) and kmd4-1 (SALK_080249) T-DNA insertion lines were obtained from the Salk T-DNA insertion collections (Alonso, et al. (2003) *Science* 301(5633):653-657), and kmd2-1 (GABI-KAT 079A01) plants were obtained from the GABI-KAT T-DNA insertion collection. The genotype of each line was confirmed by PCR-based methodology.

Cytokinin Growth and Molecular Response Analyses. Hypocotyl and root growth analyses were performed according to known methods (Argyros, et al. (2008) *Plant Cell* 20(8):2102-2116) and hypocotyl and root lengths were measured using ImageJ software (version 1.32; National Institutes of Health). Root meristem size was determined via established methods (Perilli & Sabatini (2010) *Methods Mol. Biol.* 655:177-187). The apical meristem was visualized by bright field microscopy, with tissue sectioning, fixation, and staining performed according to known methods (Chiang, et al. (2012) *Plant Physiol.* 160(1):332-348). Total RNA isolation, cDNA production, and quantitative RT-PCR (qRT-PCR) were performed via established methods (Argyros, et al. (2008) supra). Transcript abundances were calculated using the comparative CT method, with 13-TUB3 (At5g62700) as the normalized control.

Tissue Regeneration Assay. Hypocotyls from 4-day-old dark-grown seedlings were excised and transferred to 1×MS plate medium containing 0.5 mg/L 2,4-dichlorophenoxy-acetic acid (2,4-D) and 0.05 mg/L kinetin. After 4 days, hypocotyl segments were transferred to medium containing 0.2 mg/L indole-3-butyric acid (IBA) and t-zeatin ranging from 0 to 10 mg/L (Mason, et al. (2005) supra), and callus examined after 3 weeks.

Transient Expression in *Arabidopsis* Protoplasts and In Vivo Co-Immunoprecipitation Assay. *Arabidopsis* mesophyll protoplasts were isolated from mature leaves of the wild-type plants and transfected with various constructs using known methods (Kovtun, et al. (2000) *Proc. Natl. Acad. Sci. USA* 97:2940-2945). For BiFC assay, cDNA fragments were fused to plant expression vector containing either amino- or carboxy-terminal fragments of the yellow fluorescent protein (YFP$^N$ and YFP$^C$) (Walter, et al. (2004) *Plant J.* 40:428-438). Transfected protoplasts were examined with an Axioplan2 fluorescent microscope (Carl Zeiss). Co-immunoprecipitation was performed using agarose-conjugated anti-green fluorescent protein antibody (GFP-TRAP, Chromotek) following the manufacturer's protocol with slight modifications. To examine the role of the proteasome in ARR stability, protoplasts from ARR1-HA and ARR12-Myc overexpression lines were prepared and incubated for 3 hours in the presence of 10 µM MG132 (a specific, potent, reversible, and cell-permeable proteasome inhibitor) or 0.1% dimethyl sulfoxide (DMSO) as a vehicle control, and protein levels were determined by immunoblot analysis.

Plant Growth Conditions and Cytokinin Treatment. Seeds were surface-sterilized and cold-treated for 3 days in the dark at 4° C. to ensure uniform germination before being moved into the light. For molecular and physiological assays, seedlings were grown on medium containing 1× Murashige and Skoog (MS) salts with vitamins (Research Products International Corp.), 1% sucrose, and 0.8% phytoagar (Research Products International Corp.) at 22° C. under continuous white light (50 µE·m$^{-2}$·s$^{-1}$) unless specified otherwise. For long-term growth, plants were grown in an environmentally controlled chamber room at 22° C. with a 16-hour-light/8-hour-dark cycle. For the root growth assay, seedlings were grown on vertical plates with medium containing t-zeatin ranging from 0.001 to 1.0 µM, and primary root growth measured using established methods (Argyros, et al. (2008) supra). For measurement of hypocotyl length, seedlings were grown for 4 days in the dark on 0.5×MS plates containing various concentrations of t-zeatin (Kim, et al. (2006) *Proc. Natl. Acad. Sci. USA* 103(3):814-819). For the analysis of gene expression in response to cytokinin, seedlings were grown on filter paper on agar medium for 14 days under constant light (50 µE·m$^{-2}$·s$^{-1}$), then transferred to liquid MS medium containing either t-zeatin or BA, controls containing the appropriate vehicle used to dissolve the cytokinin.

Generation of Transgenic Plants. For KMD1-GFP and KMD2-GFP overexpression lines, cDNAs covering the complete coding sequence were cloned into pCR8/GW/TOPO (Invitrogen), and recombined into pEarleyGate 103 (Earley, et al. (2006) *Plant J.* 45(4):616-629). For pKMD1:GUS and pKMD2:GUS lines, ~2.0 kb of the promoter was amplified from genomic DNA, cloned into pCR8/GW/TOPO (Invitrogen), and recombined into pMDC 163 (Curtis & Grossniklaus (2003) *Plant Physiol.* 133(2):462-469). To generate antisense lines of KMD4, a full-length KMD cDNA was cloned into a pCsVMV-GFP vector in the antisense orientation (Verdaguer, et al. (1996) *Plant Mol. Biol.* 31(6):1129-1139). For 35S::ARR1-HA and 35S::ARR2-HA, full-length cDNAs of ARR1 and ARR2 without stop codon were cloned into pCB302 (Xiang, et al. (1999) *Plant Mol. Biol.* 40(4):711-717). For overexpression of ARR12, an ARR12 genomic DNA fragment was cloned into pEarleyGate 203 generating an N-terminal Myc-tagged fusion (Earley, et al. (2006) supra). The resulting binary vectors were introduced into *Agrobacterium* strain AGL1 and transformed into plants using the floral dip method (Clough & Bent (1998) *Plant J.* 16(6):735-743). To examine the effects of KMD overexpression on type-B ARR protein stability, ARR1, ARR2, and ARR12 overexpression lines were crossed to a wild-type control as well as to the KMD1GFP and KMD2-GFP overexpression lines. To examine the effects of reduced KMD expression on type-B ARR protein stability, a 35S::ARR1 transgene in the kmd1,2 background was crossed to the kmd1,2,α4 lines, with protein analysis performed on the F1 seedlings.

Yeast Two-Hybrid Assays. The DUPLEX-A™ system (OriGene Technologies) was used for yeast two-hybrid analysis of interactions. KMD cDNAs were cloned into the pGilda bait vector, which produces an in-frame fusion with the LexA DNA-binding domain. Type-B ARR coding sequences were cloned into the pJG4-5 prey vector, which produces a B42 activation domain. The yeast strain EGY48 (MATa, trp1, his3, ura3, leu2::6 LexAop-LEU2) that contains the lacZ reporter plasmid pSH18-34 was transformed with the appropriate "bait" and "prey" plasmids. Interactions were tested on 5-bromo-4-chloro-3-indolyl-p-D-galactopyranoside (X-gal) medium (Ryu, et al. (2005) *Cell* 120(3): 395-406).

Bimolecular Fluorescence Complementation Analysis. For bimolecular fluorescence complementation (BiFC) assays, the full-length of KMDs, ASK1, ARR1, ARR2, and ARR12 cDNAs as well as KMD1 and KMD2 cDNA fragments encoding KMD1F-box and KMD2F-box were fused to plant expression vectors containing either amino- or carboxy-terminal fragments of YFP (YFP$^N$ and YFP$^C$) (Walter, et al. (2004) *Plant J.* 40(3):428-438). *Arabidopsis* protoplasts were transfected as described (Kovtun, et al. (2000) *Proc. Natl. Acad. Sci. USA* 97(6):2940-2945) and incubated overnight at 22° C. under dim light (5 µE·m$^{-2}$·s$^{-1}$) and examined with an Axioplan2 fluorescent microscope (Carl Zeiss).

Co-Immunoprecipitation Assays. KMD1, Cullin1, ARR1, ARR2, and ARR12 cDNAs were inserted into a plant expression vector that containing two copies of HA tag driven by the 35SC4PPDK promoter (Sheen (1996) *Science* 274(5294):1900-1902). cDNA fragments encoding KMD1 and ASK1 were fused to GFP coding sequences controlled by the CsVMV promoter (Verdaguer, et al. (1996) supra). *Arabidopsis* mesophyll protoplasts were isolated from mature leaves of the wild-type plants and transfected with various constructs expressing HA- or GFP-tagged proteins (Kovtun, et al. (2000) supra). Protoplasts were then supplemented with the proteasome inhibitor MG132 (10 µM) and incubated overnight at 22° C. under dim light (5 µE·m$^{-2,-1}$). Cells were harvested and lysed with immunoprecipitation buffer (50 mM Tris-HCl (pH 7.5), 150 mM NaCl, 10 mM EDTA, 0.1% NONIDET P-40, 50 µM MG132, 1 mM PMSF, and protease inhibitor cocktail). The supernatant was incubated with agarose-conjugated anti-GFP antibody (GFP-TRAP, Chromotek) for 2 hours at 4° C. and the pellet fraction then washed four times with 50 mM Tris-HCl (pH 7.5), 150 mM NaCl, 10 mM EDTA, 0.1% NONIDET P-40, and protease inhibitor cocktail). The protein extracts and immunoprecipitated samples were heated at 95° C. for 5 minutes in SDS-PAGE sample loading buffer and separated on 10% SDS-PAGE gels, and transferred to PVDF membranes (Gamble, et al. (2002) *Plant Physiol.* 128(4):1428-1438). The blot was probed first with HRP-conjugated monoclonal anti-HA (Santa Cruz Biotechnology) antibody, then was stripped with 0.2 N glycine (pH 3.0) and reprobed with HRP-conjugated monoclonal anti-GFP (Santa Cruz Biotechnology) antibody.

Functional analysis of OsKMD2. For OsKMD2-GFP overexpression lines, cDNAs covering the complete coding sequence were amplified with 5'-AGA TCT ATG GGT TAC AAC GA GCT GAT TCC G-3' (SEQ ID NO:16) and 5'-AGG CCT GAT TTC TAG AAG GCA GGC GGC C-3' (SEQ ID NO:17), cloned into pCR8/GW/TO PO (Invitrogen), and recombined into pEarleyGate103. The GFP-tagged OsKMD2 protein was detected by immunoblotting using an HRP-conjugated anti-GFP antibody. The analysis of hypocotyl length, co-immunoprecipitation analyses, and western blot analyses were performed as described herein for *Arabidopsis*.

EXAMPLE 2

Cytokinin-Regulated KMD Genes Encode F-Box Proteins as Part of an SCF Complex

F-box proteins, which function as the specificity components within SCF-E3 ligases, are key regulators for several plant hormone-signaling pathways (Hua & Vierstra (2011) supra). By examining microarray data (Kiba, et al. (2005) *Plant Cell Physiol.* 46(2):339-355; Goda, et al. (2008) *Plant J.* 55(3):526-542), a cytokinin-regulated gene (At1g80440) encoding a novel F-box protein was identified. The protein encoded by At1g80440 contains an amino-terminal F-box motif followed by a Kelch-repeat domain that could mediate protein-protein interactions (Andrade, et al. (2001) *Plant Mol. Biol.* 46(5):603-614). At1g80440 was designated as KISS ME DEADLY 1 (KMD1) and its homologs At1g15670, At2g44130, and At3g59940 as KMD2, KMD3, and KMD4, respectively. Expression of three out of the four family members was cytokinin regulated, KMD1, KMD3 and KMD4 exhibited a two-fold reduction in transcript levels within one hour of cytokinin treatment. The effect of cytokinin on KMD gene expression was reduced in the type-B ARR double mutant arr1,arr12 (Mason, et al. (2005) *Plant Cell* 17(11):3007-3018), indicating the necessity of these type-B ARRs for mediating the transcriptional effect of cytokinin on KMD expression. Based on normalized microarray data from the *Arabidopsis* eFP browser (Schmid, et al. (2005) *Nat. Genet.* 37(5):501-506; Winter, et al. (2007) *PLoS One* 2(8):e718.23), KMD family members are broadly expressed with expression evident at the shoot apical meristem (especially KMD1 and KMD2) and at the root tip (especially KMD2 and KMD3), tissues where cytokinin regulates cell division (Mok (1994) In Cytokinins: Chemistry, Activity, and Function, eds Mok & Mok (Boca Raton, Fla.: CRC Press), pp 155-166; Dewitte, et al. (1999) *Plant Physiol.* 119(1):111-122).

KMD proteins contain a conserved amino-terminal F-box motif. To determine if KMDs function as canonical F-box proteins, their interactions with known components of the *Arabidopsis* SCF complex were examined. All four of the full-length KMD proteins interacted with ASK1, an *Arabidopsis* Skp1 protein of the SCF complex, in a bimolecular fluorescence complementation (BiFC) assay in protoplast cells. The F-box domains of KMD1 and KMD2 were sufficient for interaction with ASK1. The BiFC fluorescent signal was detected in both the nucleus and cytoplasm, consistent with the subcellular localization of KMD proteins, implying that KMD proteins may function as F-box proteins in the cytoplasm as well as in the nucleus. Co-immunoprecipitation analysis was performed to confirm interactions of KMD1 within an SCF complex. Both haemagglutinin (HA)-tagged KMD1 and Cullin1 co-immunoprecipitated with GFP-tagged ASK1, consistent with the KMD proteins functioning within a SCF complex in plant cells.

EXAMPLE 3

KMD Family Members Function as Negative Regulators of Cytokinin Responses

Figure 5B:
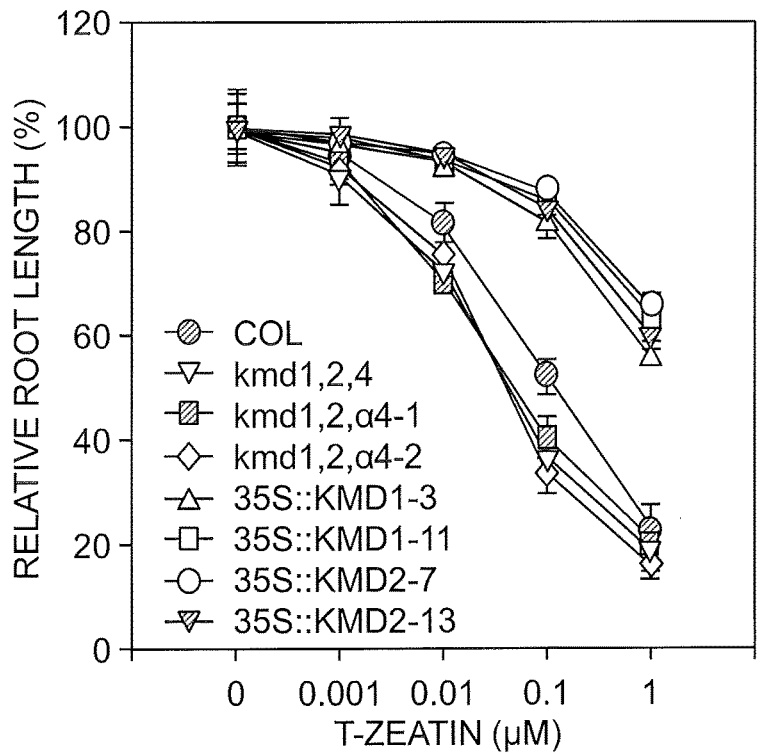

To investigate the functional role of KMDs in cytokinin signaling, mutants that harbor T-DNA (transfer DNA) insertion mutations in KMD1, KMD2, and KMD4 genes were isolated. No full-length transcripts were detected for the mutant alleles based on RT-PCR analysis, which based on the position of the T-DNA inserts, suggests that these represent null alleles. To examine the contributions of individual KMD genes to cytokinin responsiveness and their interactions, the inhibition of hypocotyl elongation of single, double, and triple mutants in response to exogenous cytokinin was examined. Single and double kmd mutants were comparable to the wild-type in this assay, whereas a kmd1-1;kmd2-1;kmd4-1 (kmd1,2,4) triple mutant showed enhanced sensitivity to cytokinin (FIG. 5A), indicating genetic redundancy among these genes. Independent antisense transgenic lines were also generated using a KMD4 antisense construct in the kmd1,2 background (kmd1,2,α4), which resulted in reduced transcript levels of both KMD3 and KMD4. The kmd1,2,α4 lines, like the kmd1,2,4 line, exhibited increased sensitivity to cytokinin in hypocotyl and root growth response assays (FIGS. 5A and 5B) as well as in the ability of cytokinin to induce greening and shoot formation in tissue-cultured explants. The effect of cytokinin on root development is in part due to a negative effect on root meristem size (Dello Ioio, et al. (2008) *Science* 322 (5906):1380-1384; Moubayidin, et al. (2010) *Curr. Biol.* 20(12):1138-1143). Consistent with this, both kmd1,2,4 and kmd1,2,α4 lines had fewer cells in their root meristems, indicating that the absence of endogenous KMD proteins mimics the effect of cytokinin by reducing the size of the root meristem.

It was confirmed that the KMD family functions as a negative regulator for cytokinin signaling by examining transgenic lines overexpressing KMD1 and KMD2 under the constitutive CaMV 35S promoter. These overexpression lines exhibited a substantially reduced cytokinin response in the several physiological assays including hypocotyl and root growth in response to cytokinin (FIGS. 5A and 5B) as well as in shoot initiation assays. Significantly, the 35S:: KMD1 and 2 lines responded normally to the ethylene precursor 1-aminocyclopropane-1-carboxylic acid (ACC) and the synthetic auxin naphthalene-1-acetic acid (NAA), indicating a specificity toward cytokinin for their effect on signaling. KMD1 and KMD2 were also expressed using the cassava vein mosaic virus (CsVMV) promoter, which yielded higher expression levels than that mediated by the CaMV 35S promoter. Seedlings of the CsVMV::KMD lines were stunted and exhibited premature termination of primary root growth. The shoot apical meristem (SAM) of the CsVMV::KMD lines exhibited a wild-type structure and organization, but was considerably smaller than that found in wild-type seedlings. In addition, the root meristem was considerably smaller in the CsVMV::KMD lines compared with wild-type, with an almost two-fold reduction in the number of cortical meristem cells. These meristematic changes resulting from overexpression of KMD1 and KMD2 are very similar to those previously reported for severe mutations in the primary cytokinin signaling pathway (Argyros, et al. (2008) supra; Nishimura, et al. (2004) *Plant Cell* 16(6):1365-1377; Hutchison, et al. (2006) *Plant Cell* 18(11):3073-3087).

To investigate whether the increase in cytokinin sensitivity of the higher order kmd mutants was associated with enhanced cytokinin signal transduction, the expression of the cytokinin primary response genes ARR7 and ARR15 was examined by qRT-POR. In wild-type plants, ARR7 and ARR15 were induced two- to four-fold by a one hour treatment with 100 nM t-zeatin. Both the kmd1,2,4 and kmd1,2,α4 lines exhibited a greater amplitude in cytokinin-induced ARR7 and ARR15 expression (four- to eight-fold) compared to the wild-type, a similar change in responsiveness to what has been found with mutations in other negative regulators of the pathway (To, et al. (2004) supra). The molecular response to cytokinin was also altered in the 35S::KMD1 and lines. The basal RNA levels of ARR7 and ARR15 were decreased compared with that in the wild-type, indicating a reduced response to endogenous cytokinin in the 35S::KMD lines. Moreover, the degree of induction of the ARR genes by cytokinin was also reduced by KMD overexpression. This molecular phenotype is similar to what has been observed with mutations in other positive regulators of the cytokinin signaling pathway (Argyros, et al. (2008) supra; Nishimura, et al. (2004) supra; Hutchison, et al. (2006) supra). Overall, these physiological and molecular results reveal that the KMD family members function as negative regulators of the cytokinin signaling pathway.

EXAMPLE 4

KMD Proteins Physically Interact with Type-B ARR Proteins

The similarity of KMD mutant phenotypes to those involving type-B ARR mutations (Argyros, et al. (2008) supra; Ishida, et al. (2008) *Plant Cell Physiol.* 49(1):47-57; Sakai, et al. (2001) *Science* 294(5546):1519-1521), indicated that these F-box proteins might target the type-B ARR proteins for degradation. To demonstrate an interaction between KMD and type-B ARR proteins, yeast two-hybrid assays were performed. The KMD proteins exhibited a strong interaction with ARR1, ARR12, and, to a lesser extent, ARR2 and ARR10, out of the seven type-B ARR members of subfamily-1 tested. The KMD proteins also interacted with ARR20 (type-B ARR subfamily-3), but not with ARR19 (subfamily-2) and ARR21 (subfamily-3). Significantly, the KMD proteins did not interact with representative members of the type-A ARRs (ARR4 and ARR7), indicating that interaction with the KMD proteins is not a general characteristic of the plant response regulators. Subsequent analysis was focused on ARR1 and ARR12 because genetic studies have demonstrated that these two type-B ARRs are major contributors to multiple cytokinin responses (Argyros, et al. (2008) supra; Mason, et al. (2005) supra). All four KMD proteins interacted with both ARR1 and ARR12 in a BiFC assay. Strong fluorescence was detected in the nuclei of cells, consistent with the subcellular localization of the type-B ARRs (Hwang & Sheen J (2001) Nature 413 (6854):383-389; Mason, et al. (2004) Plant Physiol. 135(2): 927-937). In addition, HA-tagged ARR1 or ARR12 proteins co-immunoprecipitated with a GFP-tagged KMD1 protein from extracts of transfected protoplasts. ARR2 also interacted in vivo with KMD1 even though this interaction was weaker based on the yeast-two hybrid analysis. These results indicate that multiple type-B ARRs serve as direct targets for the KMD F-box proteins. In a BiFC assay, it was found that KMD1 interacted more strongly with the C-terminal domains of ARR1 and ARR12 [ARR1 (153-669) and ARR12 (133-596)] than with their receiver domains [ARR1 (1-154) and ARR12 (1-134)]. This result indicates that the C-terminal extension of ARR1 and ARR12 is the major site of interaction with the KMD1, although N-terminal receiver domain may also contribute to a lesser extent.

EXAMPLE 5

KMD1 and KMD2 Target Type-B ARR Proteins for Degradation

It was subsequently determined whether ARR1 and ARR12 are degraded through a proteasome-dependent pathway. Protein levels of ARR1 and ARR12 increased in the presence of the proteasome inhibitor MG132, consistent with their degradation being controlled by the ubiquitin/proteasome system. Treatment with the protein biosynthesis inhibitor, cycloheximide revealed that both ARR1 and ARR12 are unstable proteins, but their turnover was not affected by exogenous cytokinin, suggesting that the lifespan of the protein may contribute to its ability to propagate the cytokinin signal. To determine if the type-B ARRs are targeted by KMDs for degradation in planta, transgenic lines expressing 35S::ARR1-HA, 35S::ARR2-HA, or 35S:: ARR12-Myc were crossed with wild-type or 35S::KMD-GFP plants, and the abundance of type-B ARR proteins in the F1 seedlings was analyzed. Elevated expression of KMD1 and KMD2 resulted in a decrease in ARR1, ARR2, and ARR12 protein levels. Furthermore, analysis of the turnover kinetics for ARR1 indicates that elevated levels of KMD1 results in an enhanced turnover rate for ARR1. In addition, it was found that the ARR1 protein is more abundant in the kmd1,2,α4 lines, thereby providing a mechanistic basis for why these lines display enhanced cytokinin sensitivity (Sakai, et al. (2001) supra). Because no changes in ARR1 and ARR12 transcript levels were observed in these lines, these results are consistent with the KMDs mediating the post-translational degradation of the type-B ARRs. To investigate whether phosphorylation of type-B ARRs is necessary for their SCF$^{KMD}$-mediated degradation in planta, ARR1$^{D89N}$ and ARR12$^{D69N}$ were generated, in which the phosphotransfer to ARR1 and ARR12 is suggested to be abolished due to mutation of the conserved Asp in the receiver domain (Imamura, et al. (2003) Plant Cell Physiol. 44:122-131; Imamura, et al. (2001) Biosci. Biotechnol. Biochem. 65(9):2113-2117). The levels of ARR1$^{D89N}$ and ARR12$^{D69N}$ decreased in the presence of overexpressed KMD1, indicating that a cytokinin-induced phosphorelay to this conserved residue is not required for the SCF$^{KMD}$-mediated degradation of ARR1 and ARR12.

EXAMPLE 6

Rice KMD2 Functions as a Negative Regulator of Cytokinin Signalling

Figure 6:
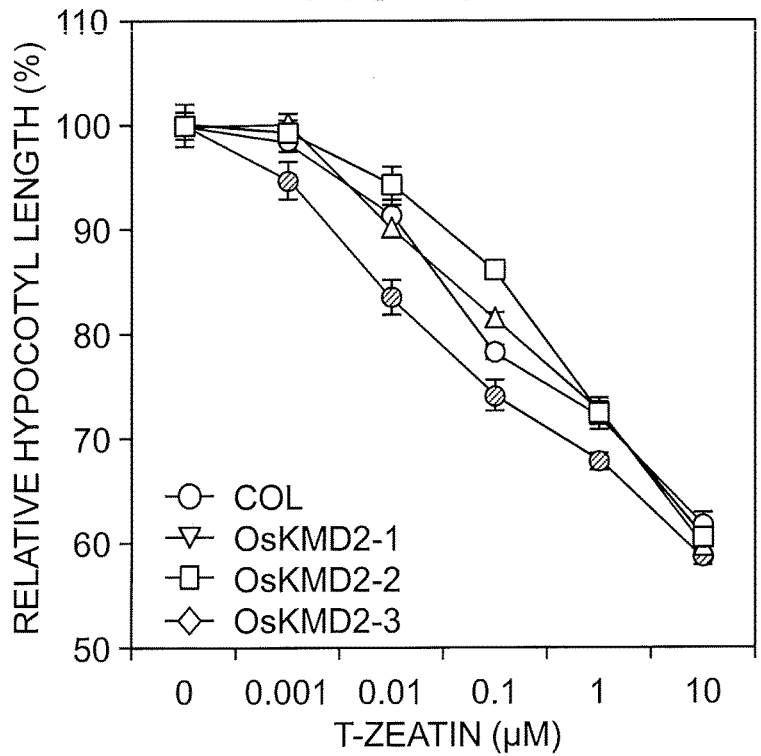
FIG. 6 shows the effect of cytokinin on hypocotyl growth of wild-type (Col) and OsKMD2 overexpression lines, OsKMD2-1, OsKMD2-2, and OsKMD2-3.

To test conservation of function between the monocot and dicot KMD genes, a cDNA clone of OsKMD2 (SEQ ID NO:5), driven by the CaMV 35S promoter and fused to a GFP reporter, was stably transformed into wild-type Arabidopsis. Multiple independent lines were generated in which the transgene was ectopically expressed to varying levels based on detection of the OsKMD2-GFP fusion by immunoblot analysis. To examine the effect of OsKMD2 on cytokinin responsiveness, these overexpression lines were examined for their inhibition of hypocotyls elongation in response to exogenous cytokinin (FIG. 6). In dark-grown, wild-type seedlings, increasing concentrations of the cytokinin t-zeatin result in an inhibition of hypocotyl elongation. All three transgenic lines exhibited a reduced cytokinin response in this growth assay compared to wild-type seedlings, the differences being most pronounced at 0.01 and 0.1 μM t-zeatin. The 35S::OsKMD2-3 line, which produced the highest level of the OsKMD2-GFP fusion protein, exhibited the strongest effect on cytokinin responsiveness (FIG. 6). The effect of the OsKMD2 gene on this growth response to cytokinin is similar to what was observed when members of the Arabidopsis KMD family were ectopically expressed. These results indicate that OsKMD2 acts as a negative regulator of cytokinin responses and support functional conservation among this gene family of monocots and dicots.

The Arabidopsis KMDs directly interact with type-B ARRs to control their degradation. To determine if the action of OsKMD2 in Arabidopsis also involved direct interaction with type-B ARRs, the ability of OsKMD2 to interact with the response regulator AtARR12 was examined using yeast two-hybrid and co-immunoprecipitation assays. Yeast two-hybrid analysis demonstrated a clear interaction between OsKMD2 and AtARR12, similar to that found with the phosphotransfer protein AtAHP2, a known interactor of type-B AtARRs (Dortay, et al. (2006) FEBS J. 273:4631-44). For co-immunoprecipitation analysis, ARR12-HA was co-transfected with either OsKMD2-GFP or GFP into Arabidopsis protoplasts. Immunoprecipitation with an anti-GFP antibody resulted in co-immunoprecipition of ARR12-HA with OsKMD2-GFP, but not with the negative control GFP, confirming the ability of OsKMD2 to directly interact with ARR12. To determine if the interaction of OsKMD2 with ARR12 affected the stability of ARR12 in planta, a transgenic line expressing 35S::ARR12-Myc was crossed with wild-type or 35S::OsKMD2-GFP plants, and the level of the ARR12-Myc protein was analyzed in the F1 seedlings. Elevated expression of OsKMD2 resulted in a decrease in the level of ARR12 protein, consistent with what was observed with the *Arabidopsis* KMD F-box proteins.

These results support a conserved function for the rice F-box protein OsKMD2 with the KMD family of F-box proteins of *Arabidopsis*, based on their shared ability to: (1) decrease cytokinin sensitivity when overexpressed; (2) directly interact with the type-B response regulator AtARR12; and (3) reduce the protein level of AtARR12 when overexpressed. Based on these functional analyses, coupled with their phylogenetic relationship, both rice and *Arabidopsis* employ 4-member families of KMD F-box proteins, which serve to regulate the transcriptional output from the cytokinin signalling pathway by targeting the type-B response regulators for degradation.

What is claimed is:

1. An expression cassette comprising a polynucleotide encoding a polypeptide of SEQ ID NO:1, SEQ ID NO:2, SEQ ID NO:4 or SEQ ID NO:5, wherein said polynucleotide is operatively linked to a heterologous regulatory element.

2. An isolated host cell comprising the expression cassette of claim 1.

3. A transgenic plant comprising the expression cassette of claim 1.

4. The transgenic plant of claim 3, wherein said plant is a dicot or monocot.

5. A transformed seed of the plant of claim 4, wherein the seed comprises the expression cassette.

6. A transgenic plant comprising a transgenic rootstock, wherein the transgenic rootstock comprises the expression cassette of claim 1.

7. A method for desensitizing a plant to endogenous cytokinin comprising introducing into a plant an expression cassette comprising a polynucleotide encoding a polypeptide of SEQ ID NO:1, SEQ ID NO:2, SEQ ID NO:3, SEQ ID NO:4 or SEQ ID NO:5 and expressing the polypeptide to desensitize the plant to endogenous cytokinin.

8. A method for increasing seed, embryo or cotyledon size or weight comprising introducing into a plant an expression cassette comprising a polynucleotide encoding a polypeptide of SEQ ID NO:1, SEQ ID NO:2, SEQ ID NO:3, SEQ ID NO:4 or SEQ ID NO:5 and expressing the polypeptide to increase seed, embryo or cotyledon size or weight.

9. The method of claim 8, wherein the polynucleotide is under control of a seed-preferred or embryo-preferred promoter.

10. The method of claim 8, wherein said method leads to an increase in yield.

11. A method for increasing the seed yield of a plant comprising introducing into a plant an expression cassette comprising a polynucleotide encoding a polypeptide of SEQ ID NO:1, SEQ ID NO:2, SEQ ID NO:3, SEQ ID NO:4 or SEQ ID NO:5 and expressing the polypeptide to increase at least one of weight of seeds, number of filled seeds or harvest index, relative to a corresponding wild type plant, thereby increasing the seed yield of a plant.

12. A method for increasing the size of the root or root meristem or formation of lateral or adventitious roots comprising introducing into a plant and expression cassette comprising a polynucleotide encoding a polypeptide of SEQ ID NO:1, SEQ ID NO:2, SEQ ID NO:3, SEQ ID NO:4 or SEQ ID NO:5 and expressing the polypeptide to increase the size of the root or root meristem or the formation of lateral or adventitious roots.

13. The method of claim 12, wherein the polynucleotide is under control of a root-preferred promoter.

\* \* \* \* \*

SEQUENCE LISTING

```
<160> NUMBER OF SEQ ID NOS: 17

<210> SEQ ID NO 1
<211> LENGTH: 354
<212> TYPE: PRT
<213> ORGANISM: Arabidopsis thaliana

<400> SEQUENCE: 1

Met Glu Leu Ile Pro Asn Leu Pro Asp Asp Val Ala Arg Glu Cys Leu
1               5                   10                  15

Leu Arg Ser Ser Tyr Gln Gln Phe Pro Val Ile Ala Ser Val Cys Arg
                20                  25                  30

Ala Trp Asn Arg Glu Val Ser Leu Ser Gln Phe Leu His Gln Arg Lys
            35                  40                  45

Ala Ser Arg His Ser Gln Glu Leu Leu Ile Leu Ser Gln Ala Arg Val
        50                  55                  60

Asp Pro Ala Gly Ser Gly Lys Ile Ile Ala Thr Pro Glu Tyr Arg Ile
65                  70                  75                  80

Ser Val Leu Glu Ser Gly Ser Gly Leu Trp Thr Glu Leu Pro Pro Ile
                85                  90                  95

Pro Gly Gln Thr Lys Gly Leu Pro Leu Phe Cys Arg Leu Val Ser Val
                100                 105                 110

Gly Ser Asp Leu Ile Val Leu Gly Gly Leu Asp Pro Ile Thr Trp Gln
            115                 120                 125

Ala His Asp Ser Val Phe Val Phe Ser Phe Leu Thr Ser Lys Trp Arg
        130                 135                 140

Val Gly Ala Thr Met Pro Gly Val Arg Arg Ser Phe Phe Gly Cys Ala
145                 150                 155                 160

Ser Asp Ser Asp Arg Thr Val Leu Val Ala Gly Gly His Asn Glu Glu
                165                 170                 175

Lys Cys Ala Leu Thr Ser Ala Met Val Tyr Asp Val Ser Glu Asp Lys
                180                 185                 190

Trp Thr Phe Leu Pro Asp Met Ala Arg Glu Arg Asp Glu Cys Lys Ala
            195                 200                 205

Val Phe His Ala Gly Arg Phe His Val Ile Gly Gly Tyr Ala Thr Glu
        210                 215                 220

Glu Gln Gly Gln Phe Ser Lys Thr Ala Glu Ser Phe Asp Val Ser Thr
225                 230                 235                 240

Trp Glu Trp Gly Pro Leu Thr Glu Asp Phe Leu Asp Asp Thr Gly Asp
                245                 250                 255

Thr Val Ser Pro Pro Thr Cys Val Ala Gly Gly Asp Leu Tyr Ala Cys
                260                 265                 270

Trp Gly Gly Asp Val Met Met Phe Leu Asn Asp Lys Trp Gln Lys Val
            275                 280                 285

Gly Gln Ile Pro Ala Asp Val Tyr Asn Val Thr Tyr Val Ala Val Arg
        290                 295                 300

Pro Gly Met Leu Ile Val Ile Gly Asn Gly Lys Ala Leu Ala Gly Tyr
305                 310                 315                 320
```

```
Gly Glu Ala Thr Val Gly Tyr Ile Cys Asp Leu Ser Ser Arg Trp
                325                 330                 335

Val Lys Leu Glu Thr His Gly Gly His Val Gln Ala Gly Cys Phe Leu
            340                 345                 350

Glu Val

<210> SEQ ID NO 2
<211> LENGTH: 359
<212> TYPE: PRT
<213> ORGANISM: Arabidopsis thaliana

<400> SEQUENCE: 2

Met Glu Leu Ile Pro Asp Leu Pro Glu Thr Val Ala Tyr Glu Cys Leu
1               5                   10                  15

Leu Arg Ser Ser Tyr Lys Gln Phe Pro Leu Met Ala Ser Val Cys Lys
                20                  25                  30

Leu Trp Gln Arg Glu Ile Ser Leu Ser Asp Phe Phe Arg His Arg Lys
            35                  40                  45

Ala Ser Gly His Ser Gln Glu Leu Val Val Leu Ser Gln Ala Arg Val
    50                  55                  60

Asp Pro Val Lys Glu Leu Val Ser Gly Asn Lys Thr Ile Pro Thr Pro
65                  70                  75                  80

Val Tyr Arg Ile Ser Val Leu Glu Leu Gly Thr Gly Leu Arg Ser Glu
                85                  90                  95

Leu Pro Pro Val Pro Gly His Ser Asn Gly Leu Pro Leu Phe Cys Arg
            100                 105                 110

Leu Val Ser Val Gly Ser Asp Leu Val Val Leu Cys Gly Leu Asp Pro
        115                 120                 125

Val Thr Trp Arg Thr Ser Asp Ser Val Phe Val Phe Ser Phe Leu Thr
    130                 135                 140

Ser Thr Trp Arg Val Gly Lys Ser Met Pro Gly Gly Pro Arg Ser Phe
145                 150                 155                 160

Phe Ala Cys Ala Ser Asp Ser Gln Arg Asn Val Phe Val Ala Gly Gly
                165                 170                 175

His Asp Glu Asp Lys Asn Ala Met Met Ser Ala Leu Val Tyr Asp Val
            180                 185                 190

Ala Glu Asp Arg Trp Ala Phe Leu Pro Asp Met Gly Arg Glu Arg Asp
        195                 200                 205

Glu Cys Thr Ala Ile Phe His Ala Gly Lys Phe His Val Ile Gly Gly
    210                 215                 220

Tyr Ser Thr Glu Glu Gln Gly Gln Phe Ser Lys Thr Ala Glu Ser Phe
225                 230                 235                 240

Asp Val Thr Thr Trp Arg Trp Ser Pro Gln Gly Glu Glu Phe Leu Ser
                245                 250                 255

Ser Glu Met Thr Met Trp Pro Pro Ile Cys Ala Ala Gly Glu Asn Gly
            260                 265                 270

Asp Leu Tyr Ala Cys Cys Arg Arg Asp Leu Met Met Met Lys Asp Asp
        275                 280                 285

Thr Trp Tyr Lys Val Gly Asn Leu Pro Ala Asp Val Cys Asn Val Ser
    290                 295                 300

Tyr Val Ala Ile Arg Arg Ser Gly Asn Leu Val Val Ile Gly Ser Ala
305                 310                 315                 320

Arg Tyr Gly Glu Pro Ser Val Gly Tyr Asn Trp Asp Met Ser Asn Ser
                325                 330                 335
```

```
Arg Trp Leu Lys Leu Glu Thr His Asp Lys Tyr Glu Gly His Val Gln
            340                 345                 350

Ala Gly Cys Phe Leu Glu Ile
            355

<210> SEQ ID NO 3
<211> LENGTH: 409
<212> TYPE: PRT
<213> ORGANISM: Arabidopsis thaliana

<400> SEQUENCE: 3

Met Thr Met Glu Val Ser Lys Lys Gly Gly Asp Phe Gln Gln Cys
 1               5                  10                  15

His Glu Leu Ile Pro Gly Leu Pro Ser Glu Leu Ala Leu Glu Cys Leu
                20                  25                  30

Val Arg Val Pro Phe Gln Phe Gln Ser Ala Met Arg Ser Val Cys Arg
            35                  40                  45

Ser Trp Arg Ser Leu Leu Ser Asp Ser Ser Phe Ile Gln Glu Arg Arg
        50                  55                  60

Arg Cys Gly Lys Thr Glu Leu Leu Cys Leu Val Gln Pro Leu Thr
 65                 70                  75                  80

Pro Pro Ile Pro Ala Ser Lys Ser Val Asp Glu Thr Leu Met Val Asp
                85                  90                  95

Glu Lys Lys Ser Glu Asp Glu Ser His Pro Arg Val Phe Cys Thr Pro
            100                 105                 110

Arg Phe Gly Leu Ser Val Tyr Asn Ala Ala Met Ser Thr Trp His Arg
        115                 120                 125

Val Ala Phe Pro Glu Glu Glu Gln Ile Pro Leu Phe Cys Glu Cys Val
    130                 135                 140

Val Leu Gln Asp Ala Gly Lys Ile Leu Leu Ile Gly Gly Trp Asp Pro
145                 150                 155                 160

Glu Thr Leu Gln Pro Thr Arg Asp Val Tyr Val Leu Glu Phe Ala Gly
                165                 170                 175

Arg Lys Trp Arg Arg Gly Ala Pro Met Lys Glu Ser Arg Ser Phe Phe
            180                 185                 190

Ala Cys Ala Ser Val Ser Pro Thr Lys Val Tyr Val Ala Gly Gly His
        195                 200                 205

Asp Asp Gln Lys Asn Ala Leu Arg Ser Ala Glu Val Tyr Asp Val Glu
    210                 215                 220

Lys Asp Glu Trp Ser Ser Val Thr Pro Met Thr Glu Gly Arg Asp Glu
225                 230                 235                 240

Cys Gln Gly Phe Ala Val Gly Met Gly Leu Arg Phe Cys Val Leu Ser
                245                 250                 255

Gly Tyr Gly Thr Glu Ser Gln Gly Arg Phe Arg Ser Asp Gly Glu Ile
            260                 265                 270

Tyr Asp Pro Ala Thr Asp Ser Trp Ser Arg Ile Asp Asn Val Trp Arg
        275                 280                 285

Phe Pro Asp Thr Ser Pro Arg Gly Arg Thr Ala Gly Asp Phe Arg Ser
    290                 295                 300

Ser Ser Thr Leu Trp Cys Phe Thr Asp Thr Asp Leu Gln Ser Glu Arg
305                 310                 315                 320

Arg Trp Glu Thr Asn Asp Asp Ser Arg Asn Leu Lys Leu Asp Leu Gln
                325                 330                 335

Ser Ile Gln Leu Pro Met Thr Gly Ser Ser Val Phe Ala Gly Ser Leu
```

```
               340                 345                 350
Gly Gly Glu Ser Val Val Met Ile Gly Gly Lys Arg Glu Ser Glu Gly
            355                 360                 365

Glu Gly Glu Gly Gly Val Met Met Lys Met Thr Thr Glu Lys Lys Met
        370                 375                 380

Gly Lys Trp Ser His His Val His Ile Pro Cys Asp Phe Ser Thr Leu
385                 390                 395                 400

Pro Phe Ser His Ala Ser Ile Tyr Val
                405
```

<210> SEQ ID NO 4
<211> LENGTH: 418
<212> TYPE: PRT
<213> ORGANISM: Arabidopsis thaliana

<400> SEQUENCE: 4

```
Met Gly Val Ser Lys Lys Ser Gly Glu Ile Arg Gly Asp Leu Ile
1               5                   10                  15

Pro Gly Leu Pro Glu Glu Leu Ala Ile Glu Cys Leu Val Arg Val Pro
            20                  25                  30

Phe Gln Phe His Ser Ser Ile Lys Ser Val Cys Arg Ser Trp Lys Cys
        35                  40                  45

Val Ile Ser Ser Arg Ser Phe Ile Lys Glu Arg Ile Gly Phe Gly Lys
    50                  55                  60

Ala Glu Ser Leu Leu Cys Leu Val Gln Pro Leu Thr Ser Pro Pro Ser
65                  70                  75                  80

Pro Ala Met Met Glu Gly Gly Glu Met Ser Gln Lys Lys Lys Glu Glu
                85                  90                  95

Glu Glu Gly Glu Ser Gln Met Thr Gln Gln Leu Leu Gln Pro Arg Ile
            100                 105                 110

Thr Gly Thr Pro Leu Tyr Gly Leu Ser Val Tyr Asn Ala Thr Leu Asp
        115                 120                 125

Thr Trp His Arg Val Ala Ile Pro Glu Arg Ile Pro Leu Phe Cys Glu
    130                 135                 140

Cys Val Ala Ile Gln Asp Ala Gly Lys Val Leu Leu Ile Gly Gly Trp
145                 150                 155                 160

Asp Pro Glu Thr Leu Gln Pro Val Arg Asp Val Phe Val Leu Asp Phe
                165                 170                 175

Phe Ala Gly Glu Gly Ser Gly Arg Arg Phe Arg Arg Gly Arg Pro Met
            180                 185                 190

Ser Ala Ala Arg Ser Phe Phe Ala Cys Ala Ser Val Gly Ser Thr Lys
        195                 200                 205

Val Tyr Val Ala Gly Gly His Asp Asp Gln Lys Asn Ala Leu Arg Ser
    210                 215                 220

Ala Glu Val Tyr Asp Val Glu Lys Asp Glu Trp Ser Met Leu Pro Pro
225                 230                 235                 240

Met Thr Glu Gly Arg Asp Glu Cys His Gly Phe Ser Met Ala Thr Asp
                245                 250                 255

Pro Gly Phe Cys Val Leu Ser Gly Tyr Gly Thr Glu Thr Gln Gly Gln
            260                 265                 270

Phe Arg Ser Asp Gly Glu Ile Tyr Asp Pro Ile Thr Asn Ser Trp Ser
        275                 280                 285

Thr Ile Glu Asn Val Trp Pro Phe Pro Asp Leu Ser Pro Arg Gly Arg
    290                 295                 300
```

Thr Ala Ala Ala Ala Ala Glu Phe Pro Gly Asp Phe Arg Gly Cys Arg
305                 310                 315                 320

Leu Trp Cys Phe Ile Asp Ser Glu Arg Gln Ser Gln Pro His Trp Glu
                325                 330                 335

Val Glu Asp Asp Ser Met Lys Trp Lys Val Ile Met Asp Thr Ile Arg
            340                 345                 350

Leu Pro Val Thr Thr Met Thr Ser Val Phe Ala Gly Ser Leu Ser Gly
            355                 360                 365

Gln Ala Val Ala Met Ile Gly Gly Gly Glu Ser Gly Thr Met
370                 375                 380

Met Val Lys Thr Thr Ala Glu Lys Asn Gly Gly Lys Trp Ser His Val
385                 390                 395                 400

Asn Thr Pro Ser Gly Phe Ser Ser Leu Pro Phe Ser Cys Ser Ser Ile
                405                 410                 415

Tyr Val

<210> SEQ ID NO 5
<211> LENGTH: 381
<212> TYPE: PRT
<213> ORGANISM: Oryza sativa

<400> SEQUENCE: 5

Met Gly Tyr Asn Glu Leu Ile Pro Gly Leu Pro Glu Glu Val Ala Arg
1               5                   10                  15

Glu Cys Leu Ile Arg Val Gly Phe Asp Gln Leu Pro Ala Val Arg Arg
            20                  25                  30

Ile Ser Arg Gln Trp Lys Ala Glu Val Glu Ser Pro Ala Tyr Asn Arg
        35                  40                  45

Leu Arg Lys Ala Glu Gly Leu Ala Arg Pro Ala Leu Ala Leu Val Gln
50                  55                  60

Ala Arg Arg Glu Leu Ala Glu Ala Gly Pro Ala Ala Asp Lys Gln Ser
65                  70                  75                  80

Ser Ala Gly Gly Val Pro Gly Asn Ser Tyr Arg Met Val Leu Leu Asp
                85                  90                  95

Pro Ala Glu Gly Arg Trp Thr Pro Leu Pro Glu Val Gly Gly Ala Ser
            100                 105                 110

Gly Ser Leu Pro Leu Phe Cys Gln Val Ala Ala Val Asp Gly Gly Val
        115                 120                 125

Glu Gly Arg Lys Arg Leu Val Val Gly Gly Trp Asp Pro Glu Thr
130                 135                 140

Trp Ala Pro Thr Asp Ser Val Leu Val Tyr Asp Phe Leu Thr Gly Ala
145                 150                 155                 160

Trp Arg Arg Gly Ala Ala Met Pro Gly Pro Arg Arg Ser Phe Phe Ala
                165                 170                 175

Cys Ala Ala Val Gly Gly Lys Val Phe Val Ala Gly Gly His Asp Glu
            180                 185                 190

Glu Lys Asn Ala Leu Arg Ser Ala Leu Ala Tyr Asp Pro Asp Ala Asp
        195                 200                 205

Ala Trp Ala Ala Leu Pro Asp Met Ala Glu Glu Arg Asp Glu Pro Arg
210                 215                 220

Gly Leu Cys Val Asp Gly Lys Phe Leu Val Val Gly Gly Tyr Pro Thr
225                 230                 235                 240

Pro Ala Gln Gly Arg Phe Val Gly Ser Ala Glu Trp Phe Asp Pro Ala
                245                 250                 255

```
Thr Ser Thr Trp Ser Ala Val Gln Glu Gly Phe Val Asp Gly Ala
            260                 265                 270

Cys Pro Arg Thr Cys Ser Ala Ala Pro Glu Ala Gly Asp Arg Met Tyr
            275                 280                 285

Met Leu Arg Asp Gly His Leu Val Ala Arg His Gly Ala Ile Ser Ser
            290                 295                 300

Ala Pro Ala Ala Trp Arg Pro Val Ala Pro Val Pro Glu Asp Ala Arg
305                 310                 315                 320

Thr Ala Ala Ala Val Ser Val Ile Pro Asp Gly Arg Val Val Val Ile
                325                 330                 335

Gly Ser Asp Cys His Gly Gly Asp Gln Thr Val Tyr Thr Leu Arg Glu
            340                 345                 350

Glu Ala Gly Lys Pro Ala Ser Trp Ala Arg Ala Pro Ala Pro Pro Glu
            355                 360                 365

Phe Ser Gly His Val Gln Ala Ala Cys Leu Leu Glu Ile
            370                 375                 380

<210> SEQ ID NO 6
<211> LENGTH: 45
<212> TYPE: PRT
<213> ORGANISM: Sorghum bicolor

<400> SEQUENCE: 6

Glu Leu Ile Pro Gly Leu Pro Asp Asp Val Ala Met Glu Cys Leu Ala
1               5                   10                  15

Arg Val Pro Ser Arg Ser His Arg Met Arg Val Cys Arg Gly
            20                  25                  30

Trp Arg Gly Thr Val Gly Ser Ala Glu Phe Arg Arg Arg
            35                  40                  45

<210> SEQ ID NO 7
<211> LENGTH: 45
<212> TYPE: PRT
<213> ORGANISM: Oryza sativa

<400> SEQUENCE: 7

Glu Leu Ile Pro Gly Leu Pro Asp Asp Val Ala Met Glu Cys Leu Ala
1               5                   10                  15

Arg Val Pro Ser Arg Ser His Arg Ala Val Arg Val Cys Arg Gly
            20                  25                  30

Trp Arg Arg Ala Ala Ala Ser Glu Ala Phe Arg Arg Arg
            35                  40                  45

<210> SEQ ID NO 8
<211> LENGTH: 46
<212> TYPE: PRT
<213> ORGANISM: Sorghum bicolor

<400> SEQUENCE: 8

Asp Leu Ile Pro Gly Ile Pro Asp Asp Val Ala Val Asp Cys Leu Ala
1               5                   10                  15

Arg Val Pro His Ala Ser His Arg Ala Met Arg Gly Val Cys Arg Gly
            20                  25                  30

Trp Arg Ser Ala Ala Ser Thr Pro Ala Phe Ala Ser Ala Arg
            35                  40                  45

<210> SEQ ID NO 9
<211> LENGTH: 46
<212> TYPE: PRT
```

```
<213> ORGANISM: Sorghum bicolor

<400> SEQUENCE: 9

Asp Leu Ile Pro Gly Ile Pro Asp Asp Val Ala Val Asp Cys Leu Ala
1               5                   10                  15

Arg Val Pro His Ala Ser His Arg Ala Met Arg Val Cys Arg Gly
            20                  25                  30

Trp Arg Ser Ala Ala Ser Thr Pro Ala Phe Ala Ser Ala Arg
        35                  40                  45

<210> SEQ ID NO 10
<211> LENGTH: 46
<212> TYPE: PRT
<213> ORGANISM: Zea mays

<400> SEQUENCE: 10

Glu Leu Ile Pro Gly Ile Pro Asp Asp Val Ala Val Asp Cys Leu Ala
1               5                   10                  15

Arg Val Pro His Ala Ser His Arg Ala Met Arg Val Cys Arg Gly
            20                  25                  30

Trp Arg Ser Ala Ala Ala Ala Pro Ala Phe Ala Ser Ala Arg
        35                  40                  45

<210> SEQ ID NO 11
<211> LENGTH: 46
<212> TYPE: PRT
<213> ORGANISM: Oryza sativa

<400> SEQUENCE: 11

Glu Leu Ile Pro Gly Met Pro Asp Asp Val Ala Val Asp Cys Leu Ala
1               5                   10                  15

Arg Val Pro His Gly Ala His Arg Ala Met Arg Val Cys Arg Gly
            20                  25                  30

Trp Arg Ser Ala Ala Ala Thr Pro Ala Phe Ala Met Ala Arg
        35                  40                  45

<210> SEQ ID NO 12
<211> LENGTH: 46
<212> TYPE: PRT
<213> ORGANISM: Arabidopsis thaliana

<400> SEQUENCE: 12

Glu Leu Ile Pro Gly Leu Pro Ser Glu Leu Ala Leu Glu Cys Leu Val
1               5                   10                  15

Arg Val Pro Phe Gln Phe Gln Ser Ala Met Arg Ser Val Cys Arg Ser
            20                  25                  30

Trp Arg Ser Leu Leu Ser Asp Ser Ser Phe Ile Gln Glu Arg
        35                  40                  45

<210> SEQ ID NO 13
<211> LENGTH: 46
<212> TYPE: PRT
<213> ORGANISM: Arabidopsis thaliana

<400> SEQUENCE: 13

Asp Leu Ile Pro Gly Leu Pro Glu Glu Leu Ala Ile Glu Cys Leu Val
1               5                   10                  15

Arg Val Pro Phe Gln Phe His Ser Ser Ile Lys Ser Val Cys Arg Ser
            20                  25                  30

Trp Lys Cys Val Ile Ser Ser Arg Ser Phe Ile Lys Glu Arg
```

```
<210> SEQ ID NO 14
<211> LENGTH: 46
<212> TYPE: PRT
<213> ORGANISM: Arabidopsis thaliana

<400> SEQUENCE: 14

Glu Leu Ile Pro Asn Leu Pro Asp Asp Val Ala Arg Glu Cys Leu Leu
1               5                   10                  15

Arg Ser Ser Tyr Gln Gln Phe Pro Val Ile Ala Ser Val Cys Arg Ala
            20                  25                  30

Trp Asn Arg Glu Val Ser Leu Ser Gln Phe Leu His Gln Arg
        35                  40                  45

<210> SEQ ID NO 15
<211> LENGTH: 46
<212> TYPE: PRT
<213> ORGANISM: Arabidopsis thaliana

<400> SEQUENCE: 15

Glu Leu Ile Pro Asp Leu Pro Glu Thr Val Ala Tyr Glu Cys Leu Leu
1               5                   10                  15

Arg Ser Ser Tyr Lys Gln Phe Pro Leu Met Ala Ser Val Cys Lys Leu
            20                  25                  30

Trp Gln Arg Glu Ile Ser Leu Ser Asp Phe Phe Arg His Arg
        35                  40                  45

<210> SEQ ID NO 16
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 16
agatctatgg gttacaacga gctgattccg                                        30

<210> SEQ ID NO 17
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 17
aggcctgatt tctagaaggc aggcggcc                                          28
```